(12) United States Patent
Mori et al.

(10) Patent No.: US 7,682,818 B2
(45) Date of Patent: Mar. 23, 2010

(54) APPARATUS FOR SEPARATING AND PURIFYING NUCLEIC ACID AND METHOD FOR SEPARATING AND PURIFYING NUCLEIC ACID

(75) Inventors: Toshihiro Mori, Asaka (JP); Yoshihiko Makino, Asaka (JP)

(73) Assignee: Fujifilm Corporation, Tokyo (JP)

( * ) Notice: Subject to any disclaimer, the term of this patent is extended or adjusted under 35 U.S.C. 154(b) by 1229 days.

(21) Appl. No.: 10/808,411

(22) Filed: Mar. 25, 2004

(65) Prior Publication Data
US 2004/0235025 A1 Nov. 25, 2004

(30) Foreign Application Priority Data

Mar. 28, 2003 (JP) .............................. 2003-090385
Mar. 28, 2003 (JP) .............................. 2003-090393

(51) Int. Cl.
C12M 1/34 (2006.01)
C12Q 1/68 (2006.01)
C12P 19/34 (2006.01)
G01N 15/06 (2006.01)
C07H 21/02 (2006.01)

(52) U.S. Cl. ..................... 435/287.2; 435/6; 435/91.1; 435/287.1; 422/68.1; 536/23.1

(58) Field of Classification Search ............. 435/6, 435/91.1, 183, 203.1, 287.1, 287.2; 422/50, 422/68.1; 536/23.1, 24.3, 24.33, 25.3
See application file for complete search history.

(56) References Cited

U.S. PATENT DOCUMENTS

| | | | | |
|---|---|---|---|---|
| 3,811,442 A | * | 5/1974 | Maroth | .................. 604/188 |
| 4,133,804 A | * | 1/1979 | Bach et al. | .................. 530/344 |
| 5,234,809 A | | 8/1993 | Boom et al. | |
| 5,378,360 A | * | 1/1995 | Huse et al. | ............... 210/198.2 |
| 5,405,951 A | | 4/1995 | Woodward | |
| 6,179,569 B1 | * | 1/2001 | Kojima et al. | ................. 417/63 |

(Continued)

FOREIGN PATENT DOCUMENTS

JP   2001-74756 A   3/2001

(Continued)

OTHER PUBLICATIONS

Figure 2 from US Patent No. 5,378,360 with the examiner's handwritings.*

*Primary Examiner*—Frank W Lu
(74) *Attorney, Agent, or Firm*—Birch, Stewart, Kolasch & Birch, LLP

(57) ABSTRACT

The present invention provides an apparatus for separating and purifying nucleic acids, which comprises: a cylindrical syringe having a leading end part in which a first opening part is formed, a base end part in which a second opening part is formed and an accommodation part between said first opening part and second opening part, the accommodation part being able to hold liquid therein; and a solid phase-holding member connected to said leading end part, a flow hole being formed at the leading end side of the solid phase-holding member; wherein a solid phase comprised of an organic polymer having a hydroxyl group on the surface thereof is accommodated in said solid phase-holding member, the solid phase being able to adsorb and desorb nucleic acids in a sample solution; and wherein a pressure sensor capable of detecting the pressure in the accommodation part is connected.

31 Claims, 8 Drawing Sheets

U.S. PATENT DOCUMENTS

| | | |
|---|---|---|
| 2002/0102563 A1 | 8/2002 | Gjerde et al. |
| 2002/0182718 A1 | 12/2002 | Malmquist |
| 2002/0192667 A1 | 12/2002 | Kojima et al. |

FOREIGN PATENT DOCUMENTS

| | | | |
|---|---|---|---|
| JP | 2002-345465 A | | 12/2002 |
| WO | WO 99/13976 | A1 | 3/1999 |
| WO | WO-01/42487 | A2 | 6/2001 |
| WO | WO 01/62976 | A1 | 8/2001 |

\* cited by examiner (a)

(b)

APPARATUS FOR SEPARATING AND PURIFYING NUCLEIC ACID AND METHOD FOR SEPARATING AND PURIFYING NUCLEIC ACID

This nonprovisional application claims priority under 35 U.S.C. §119(a) on Patent Application No. 2003-090385 filed in JAPAN on Mar. 28, 2003 and on Patent Application No. 2003-090393 filed in JAPAN on Mar. 28, 2003, the entire contents of which is hereby incorporated by reference.

TECHNICAL FIELD

The present invention relates to an apparatus for separating and purifying nucleic acids and a method for separating and purifying nucleic acids.

BACKGROUND ART

Nucleic acids are used in various forms in various fields. For example, in a field of recombinant nucleic acid technology, it is required that nucleic acids are used in the form of probes, genomic nucleic acids and plasmid nucleic acids.

Nucleic acids are also used in various methods in a diagnostic field. For example, nucleic acid probes are routinely used for the detection and diagnosis of human pathogens. Similarly, nucleic acids are used for detecting genetic disturbances. In addition, nucleic acids are also used for detecting food-contaminating substances. Further, nucleic acids are routinely used for the localization, identification and isolation of nucleic acids of interest for various reasons such as mapping, cloning and recombination expression.

In many cases, nucleic acids can only be obtained in a small quantity, and isolation and separation operations thereof are complicated and require time. These often time-consuming, complicated operations tend to lead to loss of nucleic acids. In the purification of nucleic acids in samples obtained from blood sera, urine and cultures of bacteria, the risk of resulting in contamination and a false positive will be added.

One of the widely known purification methods is a method for purifying nucleic acids by adsorbing them on the surface of silicon dioxide, silica polymers, magnesium silicate or the like, followed by operations such as washing, desorption and the like (for example, JP Patent Publication (Kokoku) No. 7-51065 B (1995)). This method is excellent in separation performance. However, industrial mass production of the adsorbents with the same performance is difficult, and also there are problems that these adsorbents are inconvenient in handling and difficult to be processed into various shapes; the method using centrifugal separation is difficult to be automated; and the like.

Moreover, a well known method for purifying nucleic acid includes a method in which nucleic acids are adsorbed on or desorbed from the solid phase by pressurizing the inside of a syringe by a piston or a pump. According to conventional methods, the inside of a syringe is pressurized and the liquid in the syringe is discharged to the outside of the syringe after a lapse of a certain time, and then next operation has been performed. However, there is a problem that the time for extruding all of the liquid in the syringe to the outside of the syringe varies depending on the properties of the liquid (particularly, viscosity of the liquid or the like). Namely, when a liquid having high viscosity is used, it takes relatively long time to extrude total amount of the liquid in the syringe. On the other hand, for a liquid having low viscosity, total amount of the liquid in the syringe can be extruded in a shorter time. Therefore, there has been a problem that when nucleic acids are simultaneously purified from many types of specimens using an automated apparatus, the operation for ensuring the discharge of the total amount of the specimen in the syringe for all kinds of liquid takes a long time, because it is necessary to set enough time to allow the total amount to be extruded even for the specimen having the highest viscosity. Further, even if enough time is set, there has been no means to prove the fact that the total amount of the specimen has been discharged without fail. Furthermore, for the automation of the apparatus, it has been necessary to monitor the fact that the total amount of the specimen in the syringe has been discharged.

Recently, there has been made an attempt that nucleic acids are separated and purified by performing the steps of (1) pressurizing a nucleic acid-containing sample solution in a container and passing the above described sample solution through a solid phase located in the container to adsorb the nucleic acid on the solid phase, (2) adding a washing solution into the container and pressuring the above described washing solution to pass through the solid phase to wash the solid phase, and (3) adding a liquid for desorbing the nucleic acid from the solid phase into the container and pressurizing the above described liquid to pass through the solid phase to recover the nucleic acid into the above described liquid. The solid phase for use in the method may include, for example, a glass filter, an organic polymer having a hydroxyl group on the surface thereof or the like. In the above steps (1) to (3), pressurizing allows the liquid in the container to be passed through the solid phase to be discharged to the outside of the container, wherein the pressure inside the container has been ever increasing by the pressurizing. However, too high pressurizing causes too high rate for extruding the liquid in the container. This leads to a problem that the liquid forms droplets in the container and the liquid in the form of droplets is left in the container.

DISCLOSURE OF THE INVENTION

An object of the present invention is to provide an apparatus for separating and purifying nucleic acids in which a method for separating and purifying a nucleic acid by adsorbing the nucleic acid in a specimen on the surface of a solid phase and desorbing it after washing and the like is achieved; a solid phase which is excellent in separation performance, has a good washing efficiency, is easy to process, has substantially the same separation performance and can be produced in large amounts is used; the operation time is reduced; and is easy to be automated. Another object of the present invention is to provide a method for separating and purifying nucleic acids using the above described apparatus for separating and purifying nucleic acids.

A further object of the present invention is to provide a method for separating and purifying nucleic acids comprising a step of pressurizing a nucleic acid-containing sample solution in a container and passing the above described sample solution through a solid phase located in the container to adsorb the nucleic acid to the solid phase, wherein it is prevented that the liquid forms droplets in the container and the liquid in the form of droplets is left in the container.

The present inventors have diligently investigated to solve the above described problems and have found that in a method for separating and purifying nucleic acids comprising a process for adsorbing and desorbing the nucleic acids on a solid phase, the nucleic acids can be rapidly separated from the sample solution containing the nucleic acids by using an organic polymer having a hydroxyl group on the surface thereof as the above described solid phase, accommodating the above described solid phase in a container with two openings, and using an apparatus for separating and purifying nucleic acids provided with a pressure sensor. Further, the present inventors have found that the above described problems can be solved by stopping pressurizing the liquid in a container when the pressure in the container reaches a certain level. The present invention has been completed based on these findings.

Thus, the present invention provides an apparatus for separating and purifying nucleic acids, which comprises:

a cylindrical syringe having a leading end part in which a first opening part is formed, a base end part in which a second opening part is formed and an accommodation part between said first opening part and second opening part, the accommodation part being able to hold liquid therein; and a solid phase-holding member connected to said leading end part, a flow hole being formed at the leading end side of the solid phase-holding member;

wherein a solid phase comprised of an organic polymer having a hydroxyl group on the surface thereof is accommodated in said solid phase-holding member, the solid phase being able to adsorb and desorb nucleic acids in a sample solution; and wherein a pressure sensor capable of detecting the pressure in the accommodation part is connected.

The first embodiment of the present invention provides the apparatus for separating and purifying nucleic acids, which comprises a piston member comprising a plunger extending from said second opening part side into said accommodation part and a liquid-tight member provided at the leading end of said plunger, wherein the liquid-tight member can be brought into close contact with the inner surface of said accommodation part and is slidable in said accommodation part.

Preferably, the piston member is further provided with a check valve that is closed when said piston member is moved to the leading end part side and that is open when said piston member is moved to the base end part side.

The second embodiment of the present invention provides the apparatus for separating and purifying nucleic acids wherein said second opening part is connected with a pump that is capable of putting the inside of the accommodation part into a pressurized state.

Preferably, a circular solid phase-supporting surface is formed on the inner surface of the leading end side of said solid phase-holding member, the solid phase-supporting surface being generally perpendicular to the longitudinal axis of said syringe; said solid phase that is formed in a circular shape is placed in a direction parallel to said solid phase-supporting surface; the leading end of the leading end part of said syringe that is formed in a circular shape is abutted to the immediate inside of the circular peripheral edge of said solid phase to press the solid phase to the side of said solid phase-supporting surface.

Preferably, the organic polymer having a hydroxyl group on the surface thereof is a surface saponification product of acetyl cellulose. More preferably, the organic polymer having a hydroxyl group on the surface thereof is a surface saponification product of triacetyl cellulose.

Preferably, the surface saponification rate of acetyl cellulose is 5% or more, and more preferably 10% or more.

The acetyl cellulose may be formed into a porous film or a non-porous film.

Preferably, there is provided an apparatus for separating and purifying nucleic acids which comprises a combination of at least two or more apparatuses for separating and purifying nucleic acids according to claim 1, wherein each independent pressure sensor is connected to each apparatus for separating and purifying nucleic acids, and the pressure in the accommodation part of each apparatus for separating and purifying nucleic acids can be independently detected.

Another aspect of the present invention provides a method for separating and purifying nucleic acids which comprises adsorbing and desorbing nucleic acids in a sample solution on a solid phase comprised of an organic polymer having a hydroxyl group on the surface thereof by using the apparatus for separating and purifying nucleic acids according to the present invention as mentioned above.

Preferably, a pressure sensor capable of detecting the pressure in an accommodation part is used to monitor the pressure in the accommodation part, and the discharge of liquid in the accommodation part is sensed by the pressure change.

Preferably, the sample solution is a solution which is prepared by adding a water soluble organic solvent to a solution obtained by treating a specimen containing a cell or a virus with a nucleic acid-solubilizing reagent.

Preferably, the nucleic acid-solubilizing reagent is a guanidine salt, a surfactant and protease.

Preferably, nucleic acids can be separated and purified by the steps of: adsorbing nucleic acids on a solid phase comprised of an organic polymer having a hydroxyl group on the surface thereof; washing the solid phase using a nucleic acid washing buffer; and desorbing the nucleic acids adsorbed on the solid phase using a liquid capable of desorbing the nucleic acids adsorbed on the solid phase.

Preferably, the nucleic acid washing buffer is a solution containing methanol, ethanol, isopropanol, n-propanol or mixture thereof in a concentration of 20 to 100% by weight.

Preferably, the liquid capable of desorbing the nucleic acids adsorbed on the solid phase is a solution having a salt concentration of 0.5 M or less.

In the present invention, nucleic acids can be separated and purified by the steps of:

(a) preparing a sample solution containing nucleic acids by using a specimen, and charging said sample solution containing nucleic acids from a second opening part into an accommodation part;

(b) pressurizing the inside of said accommodation part of the apparatus for separating and purifying nucleic acids to discharge the charged sample solution containing nucleic acids from a flow hole to bring the solution into contact with the solid phase comprised of an organic polymer having a hydroxyl group on the surface thereof;

(c) charging a nucleic acid washing buffer from said second opening part of the apparatus for separating and purifying nucleic acids;

(d) pressurizing the inside of said accommodation part of the apparatus for separating and purifying nucleic acids to discharge the charged nucleic acid washing buffer from said flow hole to bring the buffer into contact with the solid phase comprised of an organic polymer having a hydroxyl group on the surface thereof;

(e) charging a liquid capable of desorbing nucleic acids adsorbed on the solid phase comprised of an organic polymer having a hydroxyl group on the surface thereof from said second opening part of the apparatus for separating and purifying nucleic acids; and (f) pressurizing the inside of said accommodation part of the apparatus for separating and purifying nucleic acids to discharge the charged liquid capable of desorbing nucleic acids from said flow hole to desorb the nucleic acids adsorbed on the solid phase comprised of an organic polymer having a hydroxyl group on the surface thereof and discharge the nucleic acids to the outside of the apparatus for separating and purifying nucleic acids.

Preferably, in steps (b), (d) and (f), a pressure sensor capable of detecting the pressure in an accommodation part is used to monitor the pressure in the accommodation part to sense the discharge of liquid in the accommodation part by the pressure change, and next step starts after sensing the discharge of liquid.

Further another aspect of the present invention provides a method for separating and purifying nucleic acids, which comprises the steps of:

(1) pressurizing a nucleic acid-containing sample solution in a container to pass said sample solution through a solid phase located in the container to adsorb the nucleic acids on the solid phase;

(2) adding a washing solution into the container and pressurizing said washing solution to pass through the solid phase to wash the solid phase; and (3) adding a liquid for desorbing the nucleic acids from the solid phase into the container and pressurizing said liquid to pass through the solid phase to recover the nucleic acids into said liquid, wherein the pressurization of the sample solution in step (1) is stopped when the pressure inside the container reaches a certain level.

Preferably, the pressurization in step (2) and/or step (3) is stopped when the pressure inside the container reaches a certain level.

Preferably, a certain pressure is set so that no liquid remains in the container.

Preferably, a pressure sensor is used to detect that the pressure in the container has reached a certain level.

Preferably, the solid phase is a solid phase comprised of an organic polymer having a hydroxyl group on the surface thereof.

Preferably, the organic polymer having a hydroxyl group on the surface thereof is a surface saponification product of acetyl cellulose.

Preferably, the organic polymer having a hydroxyl group on the surface thereof is a surface saponification product of triacetyl cellulose.

Preferably, the surface saponification rate of acetyl cellulose is 5% or more.

Preferably, the nucleic acid-containing sample solution is a solution which is prepared by adding a water soluble organic solvent to a solution obtained by treating a specimen containing a cell or a virus with a nucleic acid-solubilizing reagent.

Preferably, the nucleic acid-solubilizing reagent is a guanidine salt, a surfactant and protease.

Preferably, the washing solution is a solution containing methanol, ethanol, isopropanol, n-propanol or mixture thereof in a concentration of 20 to 100% by weight.

Preferably, the liquid capable of desorbing the nucleic acids from the solid phase is a solution having a salt concentration of 0.5 M or less.

Preferably, adsorption and desorption of nucleic acids are performed using an apparatus for separating and purifying nucleic acids in which a solid phase is accommodated in a container having at least two openings.

Preferably, adsorption and desorption of nucleic acids are performed using an apparatus for separating and purifying nucleic acids comprising (a) a solid phase, (b) a container having at least two openings for accommodating said solid phase, (c) a pressure difference generating apparatus coupled to one of the openings of said container and (d) a pressure sensor.

BRIEF DESCRIPTION OF THE DRAWINGS

FIGS. 7(a) and 7(b) are illustrative pictures showing another embodiment of a check valve in a piston member.

In FIGS. 1 to 7, 1 is apparatus for separating and purifying nucleic acids; 3 is syringe; 5 is piston member; 7 is solid phase-holding member; 9 is leading end part of syringe; 11 is first opening part; 13 is flange part; 15 is base end part of syringe; 17 is second opening part; 18 is locking mechanism; 19 is accommodation part; 21 is taper; 23 is external thread; 25 is internal thread; 27 is liquid-guiding surface; 29 is leading end of the leading end part; 31 is plunger; 33 is O-ring; 34 is operation part; 35 is main body part; 37 is end plate; 39 is nozzle; 41 is flow hole; 43 is solid phase-supporting surface; 45 is solid phase; 46 is polypropylene sintered filter; 47 is taper; 49 is diameter-reducing part; 51 is check valve; 53 is communicating path; 55 is valve seat; 57 is valve body; and 59 is pressure sensor.

In FIG. 2, 1 denotes a container, 10 denotes a main body, 101 denotes an opening, 102 denotes a bottom face, 103 denotes a frame, 104 denotes a wall, 105 denotes a step, 121 denotes a space, 122 denotes a space, 123 denotes a space, 13 denotes a pressing member, 131 denotes a hole, 132 denotes a projection, 20 denotes a lid, 21 denotes an opening, and 30 denotes a solid phase;

BEST MODE FOR CARRYING OUT THE INVENTION

Hereinafter, components of the apparatus for separating and purifying nucleic acids of the present invention will be described in detail.

(1) Apparatus for Separating and Purifying Nucleic Acids

An apparatus for separating and purifying nucleic acids of the present invention is characterized by comprising:

a cylindrical syringe having a leading end part in which a first opening part is formed, a base end part in which a second opening part is formed and an accommodation part between the first opening part and second opening part, the accommodation part being able to hold liquid therein; and a solid phase-holding member connected to the leading end part, a flow hole being formed at the leading end side of the solid phase-holding member;

wherein a solid phase comprised of an organic polymer having a hydroxyl group on the surface thereof is accommodated in the solid phase-holding member, the solid phase being able to adsorb and desorb nucleic acids in a sample solution; and wherein a pressure sensor capable of detecting the pressure inside the accommodation part is connected.

The first embodiment of the present invention comprises a piston member provided with a plunger extending from the above second opening part side into the above accommodation part and a liquid-tight member which is provided at the leading end of the above plunger, can be brought into close contact with the inner surface of the above accommodation part and is slidable in the above accommodation part, and the pressure sensor capable of detecting the pressure inside the accommodation part is connected to the above piston member.

One example of the first aspect of the apparatus for separating and purifying nucleic acids of the present invention will be described hereinafter with reference to the drawings.

Figure 1:
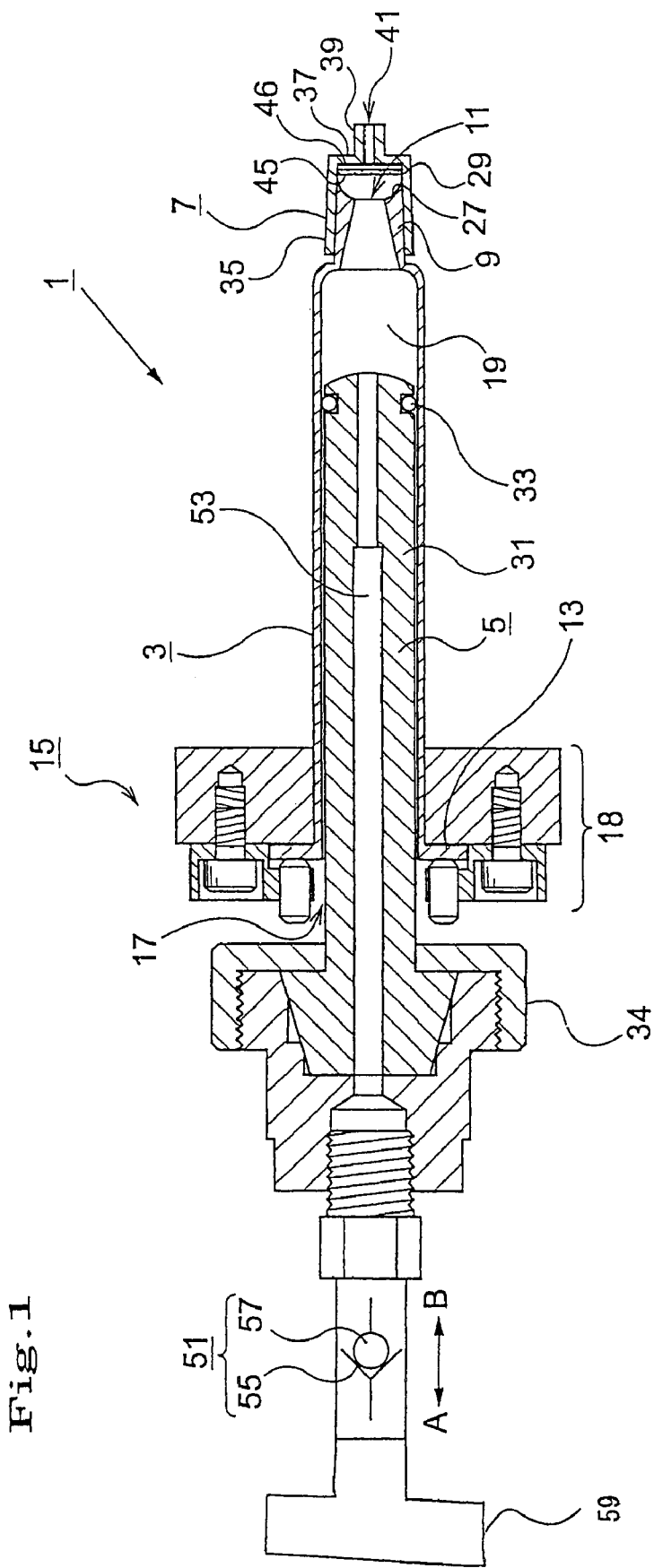
FIG. 1 is a side sectional view showing the apparatus for separating and purifying nucleic acids of the present invention and a partially enlarged view of a piston member with a check valve and a pressure sensor.

The apparatus (1) for separating and purifying nucleic acids of the present invention comprises a cylindrical syringe (3), a piston member (5) to be inserted into the syringe (3) and a solid phase holding member (7) to be connected at the leading end part of the syringe (3), as shown in FIG. 1. Note that in the present invention the side where the liquid in the syringe (3) is extruded is defined as the "leading end" side, and the opposite direction is defined as the "base end" side.

The syringe (3) has a leading end part (9) to which the phase holding member 7 is connected, and a first opening part (11) is formed in the above leading end part (9). Further, a base end part (15) in which a flange part (13) is formed is provided at the base end side of the syringe (3). In the base end part (15), a second opening part (17) is formed and a locking mechanism (18) to lock the apparatus (1) for separating and purifying nucleic acids to an appropriate locking device is provided for the flange part (13). An accommodation part (19) is formed in the syringe (3), and the accommodation part (19) can hold the liquid introduced from the first opening part (11) or the second opening part (17) by the liquid-tight action of an O-ring to be described below.

Figure 2:
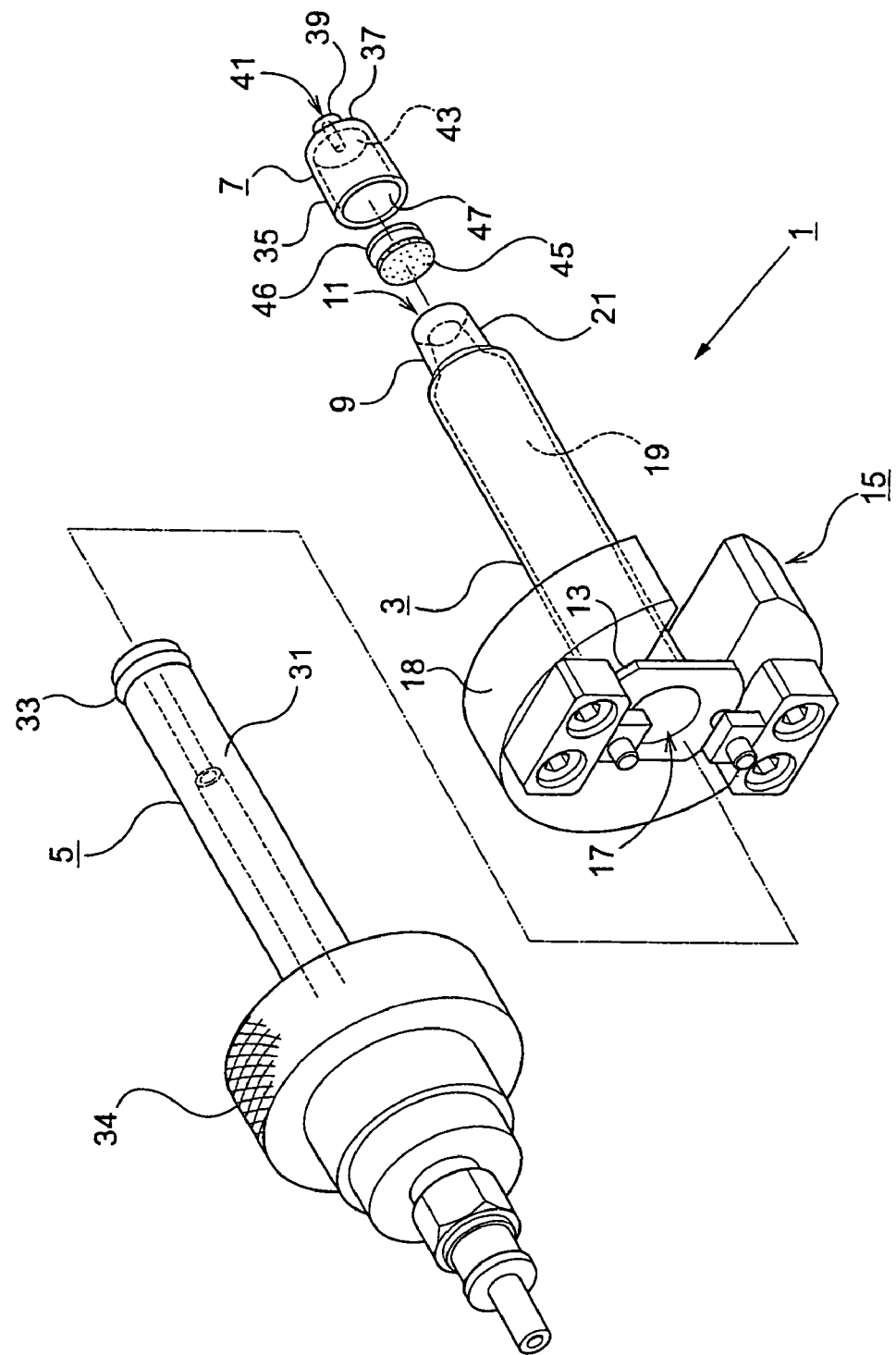
FIG. 2 is an exploded schematic view of the apparatus for separating and purifying nucleic acids of the present invention.
Figure 3:
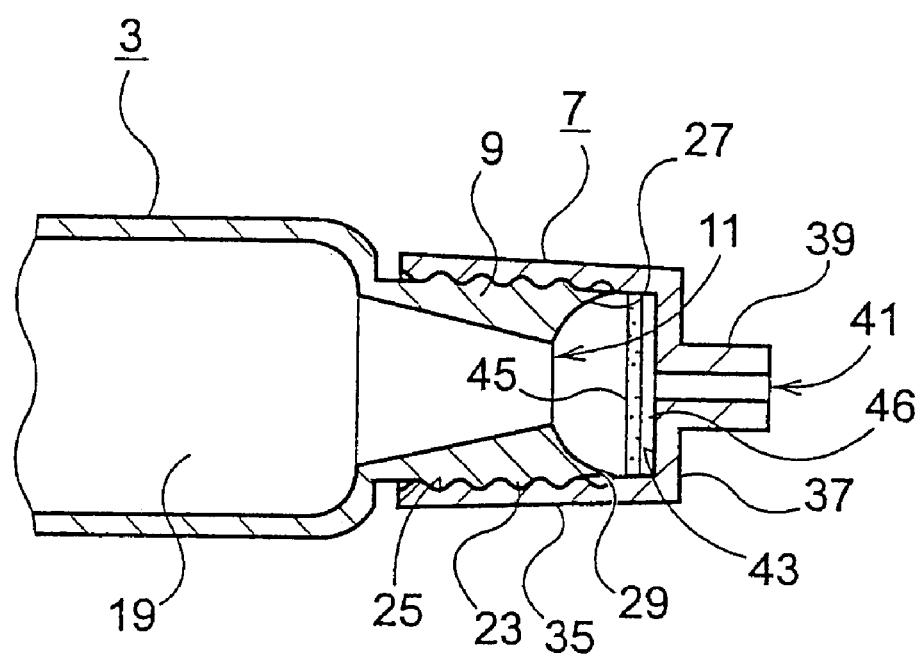
FIG. 3 is a side sectional view showing another embodiment of a method for joining a syringe and a solid phase-holding member.

As shown in FIG. 2, in the leading end part (9) of the syringe (3), there is formed a taper (21) in which the diameter of the outer peripheral surface is reduced toward the leading end so that the solid phase holding member (7) can be externally fitted. On the other hand, instead of such a taper (21), it is also possible to provide a structure in which an external thread (23) is formed on the outer peripheral surface of the leading end part (9) of the syringe (3) as shown in FIG. 3; an internal thread (25) corresponding to the external thread (23) is formed on the inner surface of the base end side of the solid phase holding member (7); and the solid phase holding member (7) is freely attachable and detachable by a screwing-type mechanism to the leading end part (9) of the syringe (3).

Figure 5:
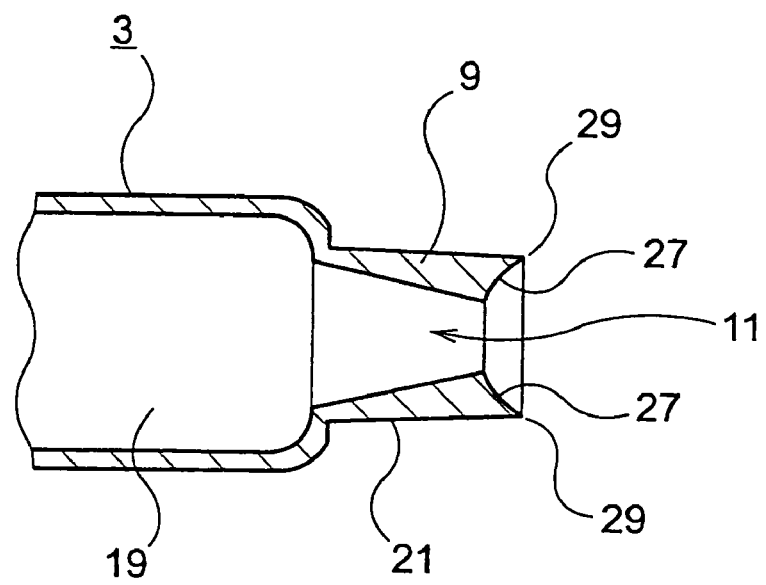
FIG. 5 is a longitudinal sectional view of the leading end part of syringe.

Further, as best shown in FIG. 5, inside the leading end part (9) of the syringe (3) is formed a liquid-guiding surface (27) having a shape in which any longitudinal cross section is curved like the curve of the second order from the leading end side toward the base end side, generally cone-shaped as a whole. The effect of the liquid-guiding surface (27) with such a shape will be described below. Further, in any longitudinal cross section of the leading end part (9) of the syringe (3), the leading end (29) of the leading end part (9) is sharp at an acute angle, which exerts the effect of holding the solid phase by press-contacting it with the surface of the solid phase comprised of an organic polymer having a hydroxyl group on the surface thereof as described below. This point will be described below in detail.

The piston member (5) comprises a plunger (31) extending from the second opening part (17) side into the accommodation part (19); an O-ring (33) which is provided around the leading end of the plunger (31), can be brought into close contact with the inner surface of the accommodation part (19) and acts as a liquid-tight member; and an operation part (34) for easily operating the plunger (31). The O-ring (33) is fixed at the leading end of the plunger (31), and so the O-ring (33) can reciprocate in the accommodation part (19) by pushing and pulling the plunger (31).

Figure 4:
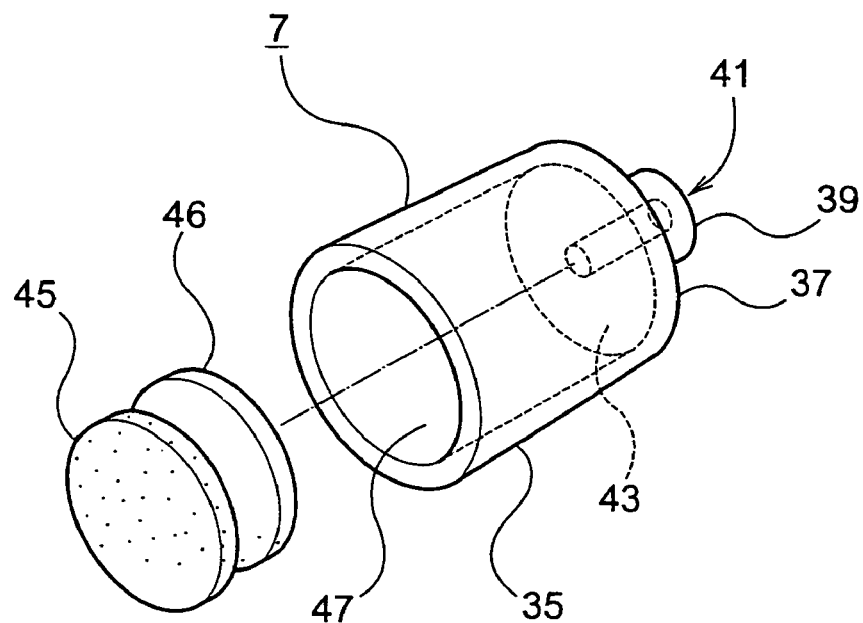
FIG. 4 is an enlarged sectional view of a solid phase-holding member.

Next, as shown in FIG. 4, the solid phase holding member (7) is mainly composed of a main body part (35) having a generally cylindrical or a little tapered shape, whose base end side is in an open state and leading end side is closed with an end plate (37). A nozzle (39) is formed at the center of the end plate (37) projecting to the leading end side, and a flow hole (41) leading to the inside of the main body part (35) is formed in the nozzle (39). On the inner surface of the end plate (37), there is formed a solid phase-supporting surface (43) which is of a circular shape and is generally perpendicular to the longitudinal axis of the syringe (3). A solid phase (45) of a circular flat plate shape comprised of an organic polymer having a hydroxyl group on the surface thereof is supported on the above solid phase-supporting surface (43). The solid phase (45) is composed of a material that can adsorb and desorb the nucleic acid in a sample solution as described in detail below.

In addition, a polypropylene sintered filter (46) providing cushioning action is provided at the leading end side of the solid phase (45). The polypropylene sintered filter (46), which has a circular flat plate shape similar to the solid phase (45), is provided between the solid phase (45) and the solid phase-supporting surface (43). Therefore, when the solid phase (45) is pressed by the leading end part (9) of the syringe (3), the polypropylene sintered filter (46) supports the solid phase (45) from the base end side thereof to provide cushioning action. This can prevent the solid phase (45) from being deformed by being excessively crushed and the space for flowing liquid formed in the solid phase (45) from being crushed to reduce the flow property of liquid.

Inside the main body part (35) of the solid phase-holding member (7), there is formed a taper (47) in which the diameter is reduced toward the leading end, corresponding to the taper (21) formed in the leading end part (9) of the above syringe (3). The taper (47) of the solid phase-holding member (7) exactly fits the outside of the taper (21) formed in the leading end part (9) of the syringe (3), and thereby the syringe (3) and the solid phase-holding member (7) can be integrated in a liquid-tight state therebetween.

When the solid phase-holding member (7) is attached to the leading end part (9) of the syringe (3), the leading end (29) with a cross section formed at an acute angle of the syringe leading end part (9) is press-contacted with the immediate inside of the circular peripheral edge of the solid phase (45) as described above. This allows the polypropylene sintered filter (46) to be in a little crushed state, so the reaction of the polypropylene sintered filter (46) having cushioning action pinches the solid phase (45) between the leading end part (9) of the syringe (3) and the polypropylene sintered filter (46). As a result, the solid phase (45) is securely supported on the solid phase-supporting surface (43) through the polypropylene sintered filter (46). By adopting a structure in which the leading end (29) with a cross section formed at an acute angle of the syringe leading end part (9) is press-contacted with the immediate inside of the circular peripheral edge of the solid phase (45) as described above, the liquid that is extruded from inside the accommodation part (19) to the outside or the liquid that flows into the accommodation part (19) through the flow hole (41), when the plunger (31) reciprocates, always passes inside the solid phase-supporting surface (43), and the liquid is prevented from flowing around the outside of the circular peripheral edge of the solid phase (45).

Figure 6:
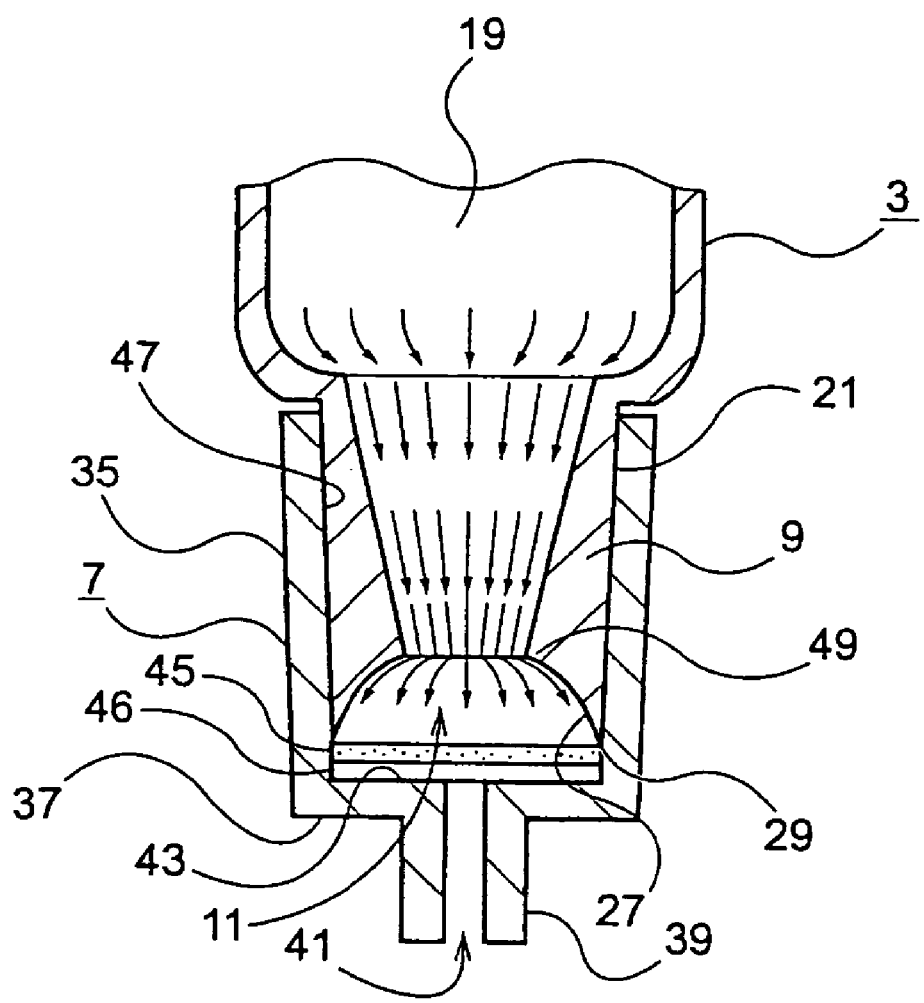
FIG. 6 is an illustrative picture showing how the liquid extruded from inside the accommodation part to the outside flows, in the leading end part of syringe.

FIG. 6 is an illustrative picture showing how the liquid extruded from inside the accommodation part (19) to the outside flows, in the leading end part (9) of the syringe (3) in which there is formed the liquid-guiding surface (27) of a shape that is curved like the curve of the second order. As shown in FIG. 6, the liquid-guiding surface (27) of a shape that is curved like the curve of the second order from a diameter-reducing part (49) that has the most reduced diameter in the leading end part (9) has a smaller rate of expansion per unit length of the diameter of the cross section, that is, the diameter-expanding rate, of the liquid-guiding surface (27) closer to the leading end side in the longitudinal axis of the syringe (3). Therefore, the diameter sharply expands around the diameter-reducing part (49), but the extent of the diameter expansion gradually becomes gentle closer to the leading end side. This structure allows the flow rate distribution in the cross section of the liquid flowing from inside the accommodation part (19) to the outside to be nearly constant in the range from the diameter-reducing part (49) to the solid phase (45), and thus nearly constant fluid pressure is applied over the entire surface of the solid phase (45). As a result, the nucleic acid-separating function, washing function and the like are effectively exerted over the entire surface of the solid phase (45) when the liquid flows between the accommodation part (19) of the syringe (3) and the outside as described below, so the separation and purification of nucleic acids can be performed efficiently.

In the apparatus for separating and purifying nucleic acids described hereinabove, the solid phase-holding member (7) is a separate member from the syringe (3), and the solid phase-holding member (7) is freely detachable and attachable to the syringe (3). However, the solid phase-holding member (7) may be locked to the syringe (3) in a state where detaching and attaching are impossible, or the solid phase-holding member (7) and the syringe (3) may be formed as an integral member from the beginning.

Next, the characteristic structure of the present invention will be described.

A pressure sensor (59) denoted by reference numeral 59 in FIG. 1 is provided in the apparatus (1) for separating and purifying nucleic acids of the present invention. The pressure sensor (59) detects the pressure change in a syringe, and thereby it is possible to determine whether all of the liquid (specimen) in the syringe is extruded or not. Further, the pressure sensor is generally coupled with means for controlling the movement of a piston. When the pressure sensor (59) detects the pressure change in the syringe, the control means for controlling the movement of the piston based on the result of the detection by the pressure sensor (59) immediately stops the movement of the piston and subsequently orders a next movement operation to the piston. The piston can perform the next movement operation based upon the order.

When nucleic acids are purified by using a conventional apparatus for separating and purifying nucleic acids which is provided with no pressure sensor, enough time to allow the total amount of liquid to be discharged even for the liquid with the highest viscosity has been set as the extrusion time (the time for pulling down the piston) for operation, because it has been unable to detect at what point in time the total amount of liquid is discharged. However, by providing the pressure sensor (59), it becomes possible to rapidly detect the point in time when all of the liquid (specimen) in the syringe is extruded depending on the types of specimens and to stop the operation for extruding the liquid (operation for pulling down the piston) at this point in time to proceed to the next operation. This allows the time required for separating and purifying nucleic acids to be reduced.

A check valve (51) denoted by reference numeral 51 in FIG. 1 is preferably provided in the apparatus (1) for separating and purifying nucleic acids of the present invention. The check valve (51) is provided at the base end side of a communication path (53) extending from the leading end of the plunger (31) to the base end side of the plunger (31) through the inside of the plunger (31), and comprises a valve seat (55) and a valve body (57) which can be brought into close contact with the valve seat (55) in a liquid-tight state. The valve seat (57) is freely movable in the longitudinal direction of the plunger (31). Therefore, when the piston member (5) is moved to the leading end part (9) side, the valve body (57) is moved in the direction of the arrow (A) and is seated on the valve seat (55) to close the check valve (51). On the other hand, when the piston member (5) is moved to the base end part (15) side, the valve body (57) is moved in the direction of the arrow (B) and apart from the valve seat (55) to open the check valve (51).

Therefore, in the apparatus (1) for separating and purifying nucleic acid shown in FIG. 1, when the piston member (5) is pressed, the liquid in the accommodation part (19) can be extruded to the outside. On the other hand, when the piston member (5) is pulled, the liquid cannot be sucked from the flow hole (41) by the action of the above check valve (51). Instead, when the piston member (5) is pulled, air is not forcefully sucked through the flow hole (41) and the solid phase (45), so the piston member (5) can easily be pulled in the direction of the base end part (15). This yields the effect that plural operations for pulling the piston member (5) can be facilitated in a step of separating and purifying nucleic acids to be described below. Further, in the step of separating and purifying nucleic acids to be described below, air is not sucked through the flow hole (41) when the piston member (5) is pulled, so pulling pressure will not act on the accommodation part (19) side. Therefore, scattering and staining of the inner wall and the piston member of the syringe (3) by the residual liquid of a sample solution containing nucleic acids and a nucleic acid washing buffer can be prevented.

Figure 7:
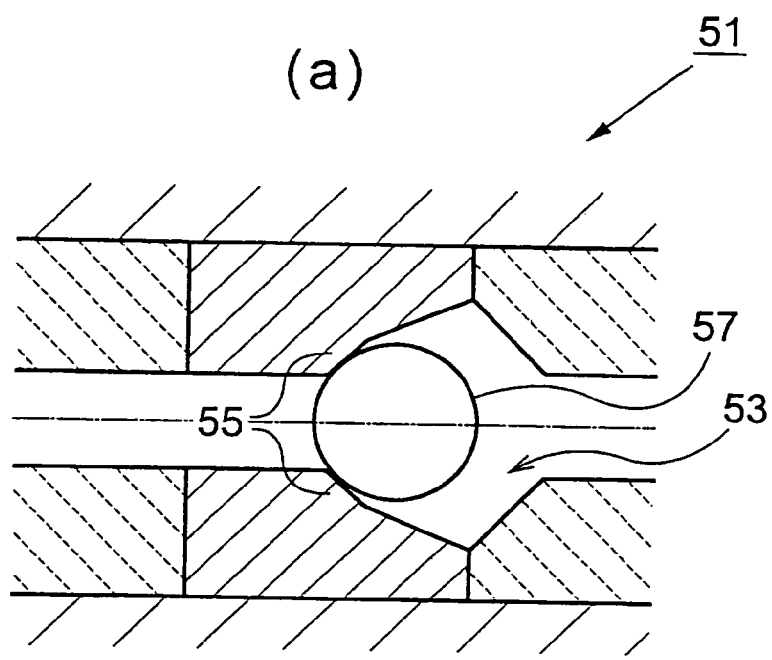
Figure 7:
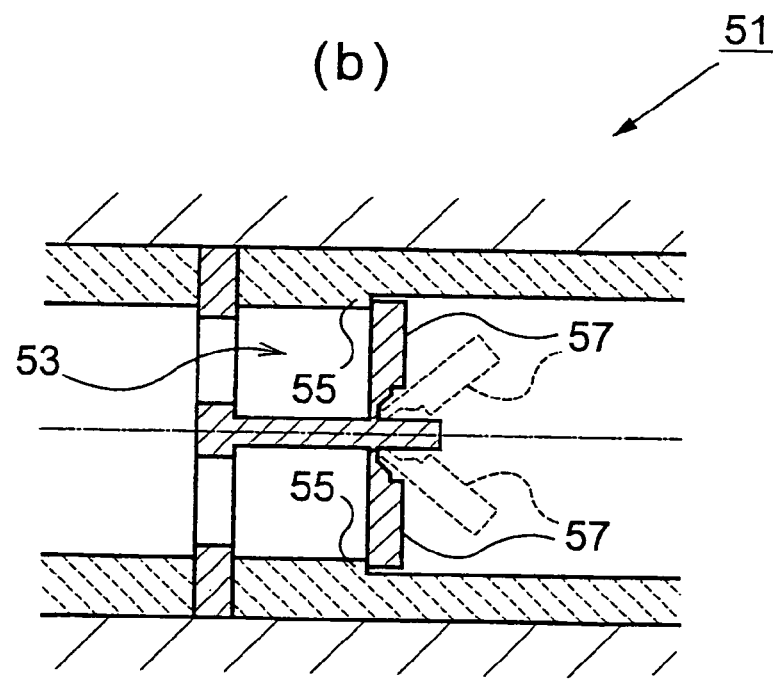

FIG. 7 shows an example of a specific structure of the check valve (51). In the example shown in FIG. 7(a), a ball-like valve body (57) faces to the valve seat (55). When the piston member (5) is pressed, the ball-like valve body (57) closes the valve seat (55). On the other hand, when the piston member (5) is pulled, the ball-like valve body (57) is apart from the valve seat (55) to open the check valve (51). Further, FIG. 7(b) shows an example in which a so-called graft hole-type check valve (51) is applied and a swingable valve body (57) is provided to the valve seat (55). In this example too, when the piston member (5) is pressed, the valve body (57) is positioned at a location indicated by the solid line in FIG. 7(b) to close the valve seat (55). On the other hand, when the piston member (5) is pulled, the valve body (57) swings to the location indicated by the broken line shown in FIG. 7(b) and is apart from the valve seat (55) to open the check valve (51).

In the second aspect of the apparatus for separating and purifying nucleic acids of the present invention, piston member is not provided. Instead of the piston member, a pump is connected to the above second opening part. The pump can be used to pressurize the inside of the accommodation part to discharge the liquid in the accommodation part.

Further, in the apparatus for separating and purifying nucleic acids of the present invention, two or more apparatuses (for example, 2 to 96 apparatuses) (for example, configurations such as 1 row×8 pieces=8 pieces, or 12 rows×8 pieces=96 pieces can be adopted) can be used in combination. In this case, the discharge of liquid can be monitored for each apparatus by providing a pressure sensor for each apparatus for separating and purifying nucleic acids. Namely, the present invention provides an apparatus for separating and purifying nucleic acids comprising a combination of at least two or more apparatuses for separating and purifying nucleic acids, wherein each independent pressure sensor is connected to each apparatus for separating and purifying nucleic acids, and the pressure in the accommodation part of each apparatus for separating and purifying nucleic acids can be independently detected.

(2) Method for Separating and Purifying Nucleic Acids

The method for separating and purifying nucleic acids of the present invention comprises a process in which the above apparatus for separating and purifying nucleic acids is used to cause nucleic acids to be adsorbed to and desorbed from a solid phase comprised of an organic polymer having a hydroxyl group on the surface thereof.

The term "nucleic acid" in the invention may be a single strand or double strand, and has no limitation of a molecular weight.

As the organic polymer having a hydroxyl group on surface thereof, surface-saponified acetyl cellulose is preferable. Acetyl cellulose may be any one of monoacetyl cellulose, diacetyl cellulose and triacetyl cellulose. Particularly, triacetyl cellulose is preferable. In the present invention, it is preferable to use surface-saponified acetyl cellulose as the solid phase. The surface saponification means that only surface to which a saponifying agent (e.g., NaOH) contacts, is saponified. In the present invention, it is preferable that a structural body of the solid phase is kept as acetyl cellulose and only the surface of the solid phase is saponified. In this way, an amount of hydroxyl groups (density) on the surface of the solid phase can be controlled according to degree of surface saponification treatment (surface saponification degree).

In order to increase surface area of the organic polymer having a hydroxyl group on the surface, it is preferable to form the organic polymer having a hydroxyl group on the surface into a membrane. Further, acetyl cellulose may be a porous membrane or a non-porous membrane. However, the porous membrane is more preferable. In the case where the solid phase is a porous membrane, it is preferable that the structural body of the membrane remains as acetyl cellulose and only the surface of the structural body is saponified. In this way, on the basis of the degree of surface saponification treatment (surface saponification degree)× the pore size, spatial amount of hydroxyl groups (density) can be controlled. Meanwhile, the structural body of the membrane is composed of acetyl cellulose and thus, a rigid solid phase can be obtained. Here, that the surface of acetyl cellulose is saponified and hydroxyl groups are introduced to the surface only, means that the structural body is kept as acetyl cellulose and the surface is converted to cellulose. When cellulose is used as a raw material, since cellulose cannot be used in liquid, the porous membrane and a flat membrane can not be manufactured industrially.

For example, the membrane of triacetyl cellulose is marketed as a commercial name TAC base from Fuji Photo Film K.K. As the porous membrane of triacetyl cellulose, there is Microfilter FM500 (Fuji Photo Film K.K.).

In addition, for example, it is also preferable to form the triacetyl cellulose membrane on the surface of polyethylene-made beads followed by surface-saponification to give hydroxyl groups to the surface. In this case, triacetyl cellulose is coated on the beads. Material of the beads may be any material which does not contaminate nucleic acids, and is not limited to polyethylene.

In order to increase efficiency of separation of nucleic acid, it is preferred to increase the number of hydroxyl groups. For example, in the case of acetyl cellulose such as triacetyl cellulose, about 5% or higher of the rate of surface saponification is preferable, and 10% or higher is more preferable.

For the surface saponification of acetyl cellulose, an object to be surface-saponified is dipped in an aqueous solution of sodium hydroxide. In order to change the surface saponification rate, the concentration of sodium hydroxide can be changed. The surface saponification rate is determined by quantifying a remaining acetyl group by NMR.

The method for separating and purifying nucleic acids according to the present invention comprises the following steps:

(a) preparing a sample solution containing nucleic acids by using a specimen, and charging said sample solution containing nucleic acids from a second opening part into an accommodation part;

(b) pressurizing the inside of said accommodation part of the apparatus for separating and purifying nucleic acids to discharge the charged sample solution containing nucleic acids from a flow hole to bring the solution into contact with the solid phase comprised of an organic polymer having a hydroxyl group on the surface thereof;

(c) charging a nucleic acid washing buffer from said second opening part of the apparatus for separating and purifying nucleic acids;

(d) pressurizing the inside of said accommodation part of the apparatus for separating and purifying nucleic acids to discharge the charged nucleic acid washing buffer from said flow hole to bring the buffer into contact with the solid phase comprised of an organic polymer having a hydroxyl group on the surface thereof;

(e) charging a liquid capable of desorbing nucleic acids adsorbed on the solid phase comprised of an organic polymer having a hydroxyl group on the surface thereof from said second opening part of the apparatus for separating and purifying nucleic acids; and (f) pressurizing the inside of said accommodation part of the apparatus for separating and purifying nucleic acids to discharge the charged liquid capable of desorbing nucleic acids from said flow hole to desorb the nucleic acids adsorbed on the solid phase comprised of an organic polymer having a hydroxyl group on the surface thereof and discharge the nucleic acids to the outside of the apparatus for separating and purifying nucleic acids.

The method for separating and purifying nucleic acids by using the organic polymer having a hydroxyl group on the surface, will be described in detail below. Preferably in the present invention, the nucleic acid in the sample solution is adsorbed to the solid phase by contacting the sample solution containing the nucleic acid to the solid phase of the organic polymer having a hydroxyl group on surface thereof, and then the nucleic acid adsorbed to the solid phase is desorbed from the solid phase by using a suitable solution described below. More preferably, the sample solution containing the nucleic acid is a solution which is obtained by adding a water-soluble organic solvent to a solution obtained by treating a cell- or virus-containing test sample with a solution capable of solubilizing a cell membrane and a nuclear membrane to disperse the nucleic acid into the solution.

The sample solution containing the nucleic acid which can be used in the present invention is not limited, but for example, in diagnostic fields, the subject solutions are the body fluid such as whole blood, serum, plasma, urine, stool, sperm and saliva which were collected as a test sample, or solutions prepared from biological materials such as plant (or a portion thereof) and animal (or a portion thereof), or their dissolved matters and homogenates.

First, these test samples are treated with an aqueous solution containing a reagent capably of lysing the cell membrane and solubilizing the nucleic acid. By this treatment, the cell membrane and the nuclear membrane are lysed, and the nucleic acid is dispersed into the aqueous solution.

For lysing the cell membrane and solubilizing the nucleic acid, for example, when the subject sample is whole blood, necessary steps are (1) removing erythrocytes, (2) removing various proteins, and (3) lysing leukocytes and lysing the nuclear membrane. (1) Removing erythrocytes and (2) removing various proteins are required to prevent non-specific adsorption to the solid phase and clogging of the porous membrane, and (3) lysing leukocytes and lysing the nuclear membrane is required to solubilize the nucleic acid which is an object of extraction. Particularly, (3) lysing leukocytes and lysing the nuclear membrane is an important step. In the method of the present invention, it is necessary to solubilize the nucleic acid in this step. For example, by incubating the sample for 10 minutes at 60° C. under the condition in which guanidine hydrochloride, Triton X100, and protease K (Sigma made) are added, the above-mentioned (1), (2) and (3) can be achieved simultaneously.

The reagent for solubilizing the nucleic acid which is used in the present invention is exemplified by the solution containing the guanidine salt, a surfactant and a protease.

The guanidine salt is preferably guanidine hydrochloride, but other guanidine salts (guanidine isothiocyanate and guanidine thiocyanate) can also be used. The concentration of guanidine salts in the solution is 0.5 M to 6 M, preferably 1 M to 5 M.

As the surfactant, Triton-X100 can be used. Alternatively, an anionic surfactant such as SDS, sodium cholate and sodium sarcosinate, a nonionic surfactant such as Tween 20 and Megafac, and other various types of amphoteric surfactants, can also be used. In the present invention, the nonionic surfactant such as polyoxyethylene octylphenyl ether (Triton X100) is preferably used. The concentration of the surfactant in the solution is normally 0.05% by weight to 10% by weight, particularly preferably 0.1% by weight to 5% by weight.

As the protease, Protease K can be used, but other proteases can also give same effect. The protease is an enzyme and thus, incubation is preferable. The protease is preferably used at 37° C. to 70° C., particularly preferably at 50° C. to 65° C.

An aqueous organic solvent is added to the aqueous solution in which the nucleic acid is dispersed, to contact the nucleic acid to the organic polymer having a hydroxyl group on the surface. By this operation, the nucleic acid in the sample solution is adsorbed to the organic polymer having a hydroxyl group on the surface. In order to adsorb the nucleic acid which was solubilized by the operation as described hereinabove to the solid phase of the organic polymer having a hydroxyl group on the surface, it is necessary that an aqueous organic solvent is mixed with the solubilized nucleic acid mixture solution, and a salt is present in the obtained nucleic acid mixture solution.

By breaking a hydrating structure of a water molecule present around the nucleic acid, the nucleic acid is solubilized in an unstable state. It is presumed that when the nucleic acid in such state is contacted to the solid phase of the organic polymer having a hydroxyl group on the surface, a polar group on the surface of the nucleic acid interacts to the polar group on the surface of the solid phase and the nucleic acid is adsorbed to the surface of the solid phase. In the method of the present invention, the state of the nucleic acid can become unstable by mixing the aqueous organic solvent with the solubilized nucleic acid mixture solution and by the presence of the salt in the obtained mixture solution of the nucleic acid.

The aqueous organic solvent used herein is exemplified by ethanol, isopropanol or propanol. Among them, ethanol is preferable. The concentration of the aqueous organic solvent is preferably 5% by weight to 90% by weight, and more preferably 20% by weight to 60% by weight. It is particularly preferable to make the concentration of ethanol to be added as high as possible in a degree in which no coagulant occurs.

As the salt present in the obtained mixture solution of the nucleic acid, various chaotropic substances (guanidium salt, sodium iodide, and sodium perchlorate), sodium chloride, potassium chloride, ammonium chloride, sodium bromide, potassium bromide, calcium bromide, ammonium bromide and the like are preferable. Particularly, guanidium salt has both effects of lysis of cell membrane and solubilization of the nucleic acid, and therefore is particularly preferable.

Subsequently, the organic polymer having a hydroxyl group on the surface to which the nucleic acid is adsorbed, is contacted to the nucleic acid-washing buffer solution. This buffer solution has a function of washing out impurities in the sample solution which are adsorbed to the organic polymer having a hydroxyl group on the surface together with the nucleic acid. Consequently, the solution should have a composition having no ability of desorbing the nucleic acid from the organic polymer having a hydroxyl group on the surface and an ability of desorbing the impurities. The nucleic acid-washing buffer solution is an aqueous solution comprising a main agent, a buffer agent and when required, a surfactant. The main agent is exemplified by an about 10 to 100% by weight (preferably about 20 to 100% by weight and more preferably about 40 to 80% by weight) aqueous solution of methanol, ethanol, isopropanol, n-propanol, butanol, acetone and the like. The buffer agent and the surfactant are exemplified by the previously described buffer agents and surfactants. Among them, a solution containing ethanol, Tris and Triton X100 is preferable. The preferable concentrations of Tris and Triton X100 are 10 to 100 mM and 0.1 to 10% by weight, respectively.

Then, to the solution capable of desorbing the nucleic acid adsorbed to the organic polymer having a hydroxyl group on the surface thereof, is contacted the washed organic polymer having a hydroxyl group on the surface as described above. This solution contains the target nucleic acid and hence, is collected and subjected to amplification of the nucleic acid by following operation, e.g., PCR (polymerase chain reaction). It is preferable that the solution capable of desorbing the nucleic acid has a low salt concentration and particularly preferably, the solution of 0.5 M or lower salt concentration is used. For this solution, purified distilled water, TE buffer and the like can be used.

(3) Method for Separating and Purifying Nucleic Acids Using an Apparatus for Separating and Purifying Nucleic Acids As an example of the present invention, a method for purifying nucleic acids using the apparatus for separating and purifying nucleic acids according to FIGS. 1 to 6 will be described. First, a sample solution containing nucleic acids is charged into the accommodation part (19) from the second opening part (17) using a pipette or the like in a state where the piston member (5) is removed from the second opening part (17). Then, the piston member (5) is inserted into the second opening part (17) to pressurize the inside of the accommodation part (19) to discharge the charged sample solution from the flow hole (41). In this discharge process, the nucleic acids in the sample solution is adsorbed on the solid phase (45) comprised of an organic polymer having a hydroxyl group on the surface thereof.

Next, the piston member (5) is removed from the second opening part (17) again and a nucleic acid washing buffer is charged from the second opening part (17). Then, the piston member (5) is again inserted into the second opening part (17) to pressurize the inside of the accommodation part (19) to discharge the charged nucleic acid washing buffer from the flow hole (41) to wash the inside of the accommodation part (19).

The nucleic acid washing buffer has a function of rinsing the sample solution remaining in the accommodation part and also rinsing impurities in the sample solution adsorbed on the solid phase together with nucleic acids. Therefore, it needs to have a composition to cause nucleic acids not to be desorbed from the solid phase (45), but to cause impurities to be desorbed from the same. A nucleic acid washing buffer is comprised of an aqueous solution consisting of a base agent, a buffer, and as necessary a surfactant. The base agent includes an aqueous solution in a concentration of about 10 to 90% (preferably about 50 to 90%) of methyl alcohol, ethyl alcohol, butyl alcohol, acetone or the like. The buffer and surfactant include buffers and surfactants described above. Among them, a solution containing ethyl alcohol, Tris and Triton-X100 is preferred. Preferred concentrations of Tris and Triton-X100 are from 10 to 100 mM and from 0.1 to 10%, respectively.

Then, the piston member (5) is again removed from the second opening part (17), and a liquid that can desorb the nucleic acids adsorbed on the solid phase (45) is charged from the second opening (17). And the piston member (5) is inserted into the second opening part (17) to pressurize the inside of the accommodation part (19) to discharge the charged liquid that can desorb nucleic acids from the flow hole (41). The discharged solution contains the nucleic acid of interest. Therefore, this solution is recovered and can be provided to subsequent operations, for example, the amplification of nucleic acids by PCR (polymerase chain reaction).

(4) Method for Separating and Purifying Nucleic Acids of the Present Invention (with Stop of Pressurization)

The method for separating and purifying nucleic acids of the present invention is characterized by comprising the steps of (1) pressurizing a nucleic acid-containing sample solution in a container to pass the above sample solution through a solid phase located in the container to adsorb the nucleic acids to the solid phase, (2) adding a washing solution into the container and pressurizing the above washing solution to pass through the solid phase to wash the solid phase, and (3) adding a liquid for desorbing the nucleic acids from the solid phase into the container and pressurizing the above liquid to pass through the solid phase to recover the nucleic acids into the above liquid, particularly, wherein pressurization of the sample solution in step (1) is stopped when the pressure inside the container reaches a certain level. In the present invention, preferably, the pressurization of not only in step (1), but also in step (2) and/or step (3) is also stopped when the pressure inside the container reaches a certain level. Further, it is preferred that the certain level of the pressure to be stopped is set so that no liquid remains in the container.

The means for stopping the pressurization at a point in time when the pressure inside a container reaches a certain level includes connecting a pressure sensor that can monitor the pressure in the container to the container. The pressure sensor is used to monitor the pressure in the container and the pressurization is continued for discharging the liquid in the container. Then, the pressurization may be stopped at a point in time when the pressure in the container that has reached a certain preset pressure is detected. In order to automate this operation, separation and purification of nucleic acids can be performed, for example, using an apparatus for separating and purifying nucleic acids comprising (a) a solid phase, (b) a container having at least two openings for accommodating said solid phase, (c) a pressure difference generating apparatus coupled to one of the openings of said container and (d) a pressure sensor. In this case, the pressure sensor for monitoring the pressure in the container is coupled to the pressure difference generating apparatus for pressurizing the inside of the container. When the above pressure sensor detects the pressure in the container that has reached a certain preset pressure, it sends a signal for stopping the pressurizing to the pressure difference generating apparatus, and thereby the pressurizing in the container can be stopped.

The solid phase used in the method as mentioned above is not particularly limited so long as nucleic acids can be adsorbed and desorbed. For example, a solid phase comprised of a glass filter or an organic polymer having a hydroxyl group on the surface thereof can be used. Preferred is a solid phase comprised of an organic polymer having a hydroxyl group on the surface thereof. The organic polymer having a hydroxyl group on the surface thereof as mentioned in (2) hereinabove can be used.

In the method for separating and purifying nucleic acids as mentioned above, prefereably, adsorption and desorption of nucleic acids can be performed using an apparatus for separating and purifying nucleic acids in which a solid phase is accommodated in a container having at least two openings.

More preferably, adsorption and desorption of nucleic acids can be performed using an apparatus for separating and purifying nucleic acids comprising (a) a solid phase, (b) a container having at least two openings for accommodating said solid phase, (c) a pressure difference generating apparatus coupled to one of the openings of said container and (d) a pressure sensor.

In this case, the method for separating and purifying nucleic acids according to the present invention comprises the following steps;

(a) preparing a sample solution containing the nucleic acid using a test sample and injecting said sample solution containing the nucleic acid into one opening of the apparatus for separation and purification of nucleic acid;

(b) making the inside of the container in the pressurized condition by using the pressure difference-generating apparatus connected to said one opening of the apparatus for separation and purification of nucleic acid, and discharging the injected sample solution containing the nucleic acid from the other opening to contact the sample solution to the solid phase;

(c) injecting the nucleic acid washing buffer into said one opening of the apparatus for separation and purification of nucleic acid;

(d) making the inside of the container in the pressurized condition by using the pressure difference-generating apparatus connected to said one opening of the uni for separation and purification of nucleic acid, and discharging the injected nucleic acid washing buffer from said other opening to contact the nucleic acid washing buffer to the solid phase;

(e) injecting the liquid capable of desorbing the nucleic acid adsorbed to the solid phase into said one opening of the apparatus for separation and purification of nucleic acid; and (f) making the inside of the container in the pressurized condition by using the pressure difference-generating apparatus connected to said one opening of the apparatus for separation and purification of nucleic acid, and discharging the liquid capable of desorbing the injected nucleic acid from said other opening, so as to desorb the nucleic acid adsorbed to the solid phase and discharge the nucleic acid to the outside of the container.

The method for separating and purifying nucleic acids as mentioned above can be carried out as mentioned in the above (2).

The apparatus for separation and purification of nucleic acids which is used in the invention is an apparatus for separation and purification of nucleic acid wherein the solid phase is contained in the container having at least two openings.

The material of the container is not particularly limited, so long as the solid phase can be contained therein and at least two openings can be provided. In view of easiness of manufacturing, a plastic is preferable. For example, clear or opaque resins such as polystyrene, polymethacrylate ester, polyethylene, polypropylene, polyester, nylon, or polycarbonate are preferably used.

Figure 8:
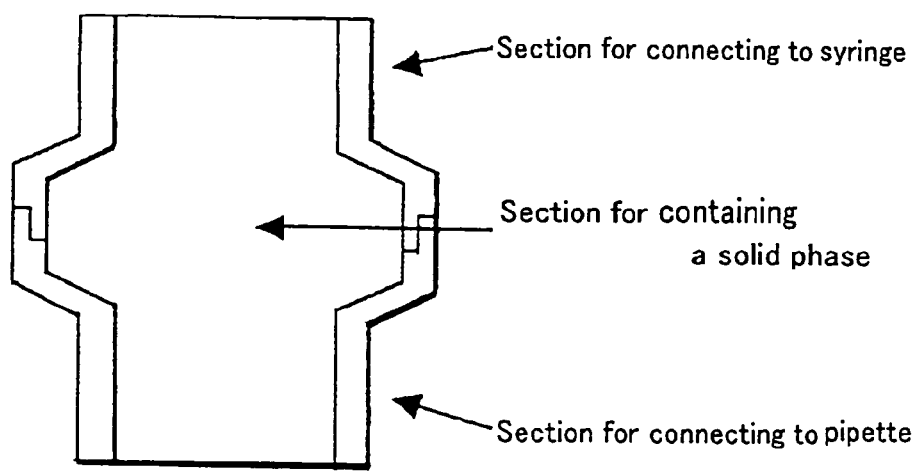
FIG. 8 is a conceptual diagram of an apparatus for separating and purifying nucleic acids of the present invention.

FIG. 8 shows a conceptual diagram of the container. Basically, the container has a section for containing the solid phase, and the solid phase is contained said containing section. The solid phase does not move out of the containing section at the time of sucking and discharging the sample solution and the like. A pressure difference-generating apparatus, e. g., a syringe, is connected to the opening. For this purpose, it is preferable that the container is initially divided into two sections, and after the solid phase is contained, these portions are integrated. In addition, in order to prevent that the solid phase moves out of the containing section, a mesh made of the material which does not contaminate DNA, can be placed on the top and the bottom of the solid phase.

The apparatus for separating and purifying nucleic acids for used in the present invention preferably comprises a pressure sensor for monitoring the pressure in the container. Namely, the pressure sensor is coupled to the pressure difference generating apparatus for pressurizing the inside of the container. When the above pressure sensor detects the pressure in the container that has reached a certain preset pressure, it sends a signal for stopping the pressurization to the pressure difference generating apparatus, and thereby the pressurization in the container can be stopped.

There is no limitation on the shape of the organic polymer having a hydroxyl group on the surface which is contained in the container as described above. The shape may be any shape such as discoid, squared, rectangular or ellipsoid; and in the membrane, cylindrical, roll, or beads coated with the organic macromolecule having a hydroxyl group on the surface. In view of manufacturing suitability, the shape having symmetric property such as discoid, squared, cylindrical and roll, and beads are preferable.

The apparatus for separation and purification of nucleic acid used in the invention preferably comprises (a) a solid phase, (b) a container containing the solid phase and having at least two openings, (c) a pressure difference-generating apparatus connected to one opening of the container, and (d) a pressure sensor. The apparatus for separation and purification of nucleic acid will be described below.

The container is normally made in a divided form of a main body which contains the solid phase (preferably, a solid phase comprised of the organic polymer having a hydroxyl group on the surface), and a lid, wherein each has at least one opening. The one is used as an inlet and an outlet of the sample solution containing the nucleic acid, the nucleic acid-washing buffer solution, a liquid capable of desorbing the nucleic acid adsorbed to the solid phase (hereinafter referred to as "sample solution and the like"); and the other is connected to the pressure difference-generating, apparatus capable of making the inside of the container in a reduced pressure or pressurized state. There is no limitation of the shape of the main body. In order to make manufacture easy and also make entire diffusion of the sample solution on the solid phase easy, it is preferable that the section is a circular shape. In order to prevent a cutting wastage of the solid, it is also preferable that the section is a squared shape.

It is necessary to connect the lid to the main body so as to make the inside of the container in the reduced pressure state or the pressurized state by using the pressure difference-generating apparatus. If this state is accomplished, the method of connection can be selected freely. For example, use of an adhesive, screwing, fitting, securing, and fusing by ultrasonic heating, are exemplified.

An internal volume of the container is determined only by an amount of the sample solution to be treated. Normally, it is expressed by the volume of the solid phase to be contained. It is preferable to use a size suitable for containing 1 to 6 sheets of the solid phase having about 1 mm or smaller (e. g., around 50 to 500 μm) thickness and about 2 mm to 20 mm diameter.

It is preferable to make an end of the solid phase to contact closely to an inner wall face of the container to prevent the sample solution and the like from being passed.

The bottom surface of the solid phase that is located oppositely to the opening used as the inlet of the sample solution and the like, is not closely contacted to the inner wall of the container, and a space is provided. Thereby, a structure suitable for achieving diffusion of the sample solution and the like evenly as possible on the entire surface of the solid phase, can be formed.

It is preferable to provide a member having a hole in generally a center thereof on the solid phase located oppositely to the other opening, i. e., the opening connected to the pressure difference-generating apparatus. This member pushes the solid phase, and has an efficient effect of discharging the sample solution and the like. This member has preferably a shape having a slope such as a funnel or a cup in such a way that the liquid is collected in the center hole. The size of this hole, an angle of the slope, and the thickness of the member can be properly determined by those skilled in the art in consideration of the amount of the sample solution and the like to be treated and the size of the container for containing the solid phase. Between this member and the opening, a space is preferably provided to store the overflowed sample solution and the like and prevent the sample solution from being sucked into the pressure difference-generating apparatus. The volume of this hole can be properly chosen by those skilled in the art. In order to collect efficiently the nucleic acid, it is preferable to suck the sample solution containing the nucleic acid in an amount which is sufficient for dipping a whole of the solid phase.

In order to prevent the sample solution and the like from being concentrated only beneath the opening through which sucking is carried out and to allow the sample solution and the like to be passed through the solid phase, a space is preferably provided between the solid phase and this member. For this purpose, it is preferable to provide a plurality of projection from the member to the solid phase. The size and number of the projection can be properly chosen by those skilled in the art. It is preferable to make an opening area of the solid phase as large as possible while keeping the space.

When the container has 3 or more openings, in order to make possible sucking and discharging the liquid by pressure-reducing and pressuring operations, it is needless to say that an excess opening should be closed temporarily.

The pressure difference-generating apparatus is exemplified by the syringe, pipetter, or a pump capable of sucking and pressurizing such as a peristaltic pump. Among them, the syringe is suitable for manual operation and the pump is suitable for automatic operation. The pipetter has an advantage of one hand operation. Preferably, the pressure difference-generating apparatus is releasably connected to the one opening of the container.

Figure 9:
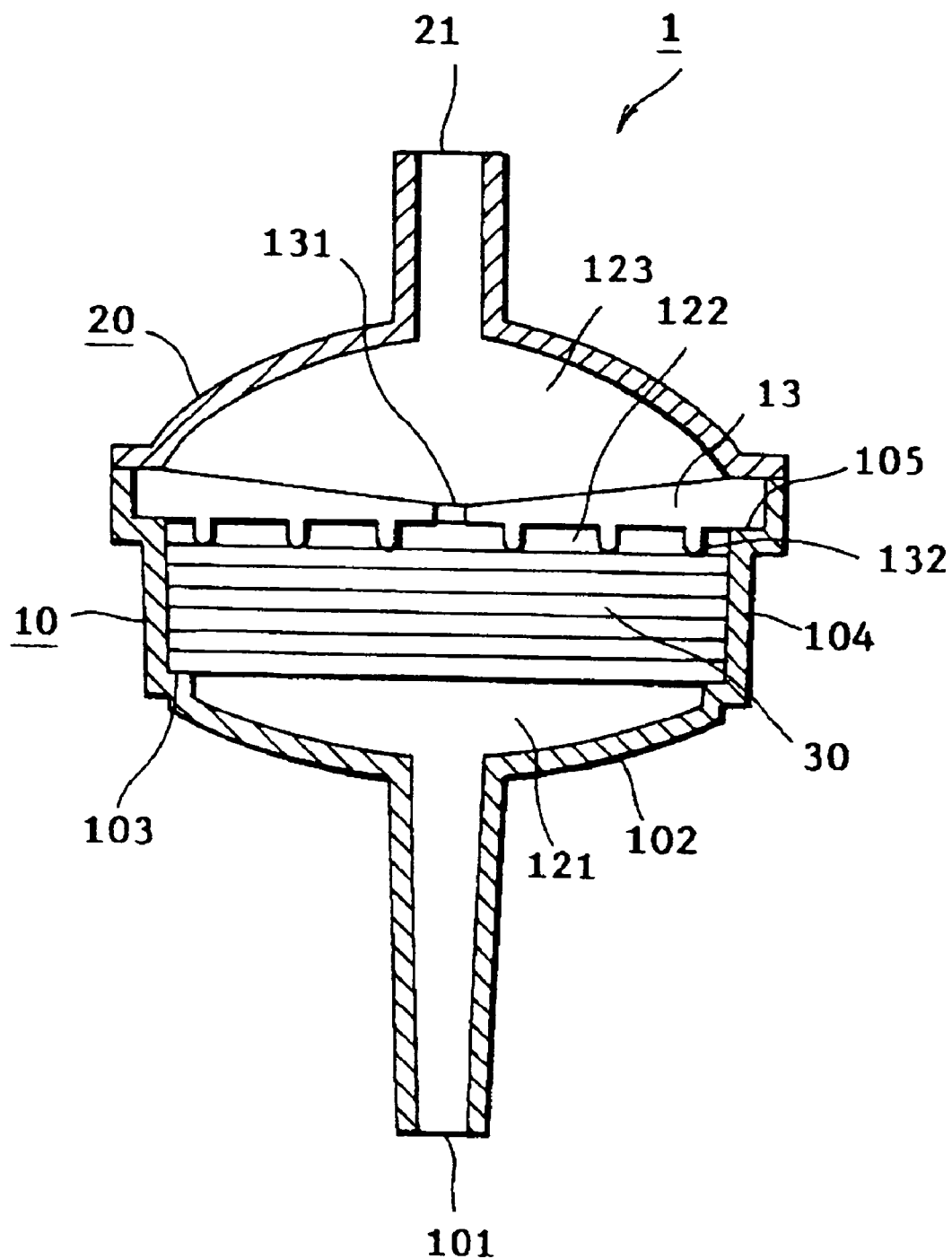
FIG. 9 is an example of the unit for separation and purification of nucleic acid according to the present invention, wherein the pressure difference-generating apparatus to be connected to the opening 21 is not illustrated.

FIG. 9 is a sectional view of an example of the apparatus for separation and purification of nucleic acid according to the present invention, provided that no pressure difference-generating apparatus is illustrated. A container (1) containing the solid phase comprises a main body (10) and a lid (20) and is made of clear polystyrene. The main body (10) contains saponified triacetyl cellulose membrane as a solid phase (30). In addition, it has an opening (101) for sucking the sample solution and the like. A bottom face (102) extending from the opening is formed in a funnel shape, and a space (121) is formed between this and the solid phase (30). In order to support the solid phase (30) and hold the space (121), a frame (103) which is formed with the bottom face (102), is provided.

The main body has an inner diameter of 20.1 mm, a depth of 5.9 mm, and a length from the bottom face (102) to the opening (101) of about 70 mm. The solid phase (30) which is contained has a diameter of 20.0 mm. The thickness of one sheet of the solid phase is about 50 to 500 µm, and an example of the thickness is 100 µm.

In FIG. 9, a funnel-shaped pressing member (13) is provided on the top of the solid phase. A hole (131) is made in a center of the pressing member (13), and a group of projections (132) are provided downward, and a space (122) is formed between this and the solid phase (30). To prevent leaking of the sample solution and the like from a space between the solid phase (30) and a wall (104) of the main body (10), the inner diameter of the upper portion of the wall (104) is larger than the diameter of the solid phase. The periphery of the pressing member (13) is mounted on a step (105).

A lid (20) is connected to the main body (10) by ultrasonic heating. In almost central part of the lid (20) is provided an opening (21) for connecting the pressure difference-generating apparatus. Between the lid (20) and the pressing member (13) is provided a space (123) for holding the sample solution and the like which flow out from the hole (131). A volume of the space (123) is about 0.1 mL.

(5) Method for Analyzing Nucleic Acids Utilizing the Apparatus for Separating and Purifying Nucleic Acid and the Method for Separating and Purifying Nucleic Acid According to the Present Invention According to the present invention, nucleic acids can be analyzed by the steps of:
(1) separating and purifying nucleic acid fragments containing target nucleic acid fragments by the above described method for separating and purifying nucleic acids;
(2) allowing the target nucleic acid fragment, at least one primer complementary to a portion of the target nucleic acid fragment, at least one deoxynucleoside triphosphate, and at least one polymerase to react with each other, and conducting polymerase elongation reaction by using the target nucleic acid fragment as a template and using 3' terminal of the primer as an initiation site; and
(3) detecting whether polymerase elongation reaction proceeds, or whether the polymerase elongation reaction product hybridizes with another nucleic acid.

According to a preferable embodiment of the present invention, whether polymerase elongation reaction proceeds can be detected by assaying pyrophosphoric acid which is produced in accordance with polymerase elongation reaction.

According to a further preferable embodiment, pyrophosphoric acid is analyzed by a colorimetric method, more preferably by use of a dry analytical element. According to the method of analyzing nucleic acid according to the present invention, it is possible to detect the presence or abundance of a target nucleic acid fragment, or to detect nucleotide sequences of the target nucleic acid fragment. The concept of the expression "to detect the abundance" used herein includes the quantification of the target nucleic acid fragment. Examples of the detection of nucleotide sequences of the target nucleic acid fragment include detection of mutation or polymorphism of the target nucleic acid.

A first preferable embodiment of the method of analyzing a target nucleic acid fragment according to the present invention is described hereinafter.
(a) The detection of pyrophosphoric acid is carried out using a dry analytical element for quantitative assay of pyrophosphoric acid which contains a reagent layer comprising xanthosine or inosine, pyrophosphatase, purine nucleoside phosphorylase, xanthine oxidase, peroxidase and a color developer.
(b) A polymerase used therein is one selected from the group consisting of DNA polymerase I, Klenow fragment of DNA polymerase I, Bst DNA polymerase, and reverse transcriptase.

Further, according to another embodiment of the present invention, when whether polymerase elongation reaction proceeds is determined by the detection of pyrophosporic acid which is produced in the polymerse elongation reaction, pyrophosphoric acid is enzymatically converted into inorganic phosphorus. Thereafter, for the detection of pyrophosphoric acid, used is a dry analytical method for quantitative assay of inorganic phosphorus which contains a reagent layer comprising xanthosine or inosine, purine nucleoside phosphorylase, xanthine oxidase, peroxidase and a color developer. A preferable embodiment for this case is described hereinafter.
(a) Pyrophosphatase is used as an enzyme for the conversion of pyrophosphoric acid.
(b) A polymerase used therein is one selected from the group consisting of DNA polymerase I, Klenow fragment of DNA polymerase I, Bst DNA polymerase, and reverse transcriptase.

The method for analyzing nucleic acids according to the present invention will be described in more detail in the following.
(A) Target nucleic acid fragment: A target nucleic acid fragment to be analyzed in the present invention is polynucleotide, at least a part of its nucleotide sequence being known, and can be a genomic DNA fragment isolated from all the organisms including animals, microorganisms, bacteria, and plants. Also, RNA or DNA fragment which can be isolated from viruses and cDNA fragment which is synthesized using mRNA as template, can be analyzed. Preferably, the target nucleic acid fragment is purified as highly as possible, and an extra ingredient other than a nucleic acid fragment is removed. For example, when a genomic DNA fragment isolated from blood of animal (e.g., human) or nucleic acid (DNA or RNA) fragments of infectious bacteria or virus existing in blood are analyzed, cell membrane of leucocyte which was destructed in the isolation process, hemoglobin which was eluted from erythrocytes, and other general chemical substances in blood should be fully removed. In particular, hemoglobin inhibits the subsequent polymerase elongation reaction. Pyrophosphoric acid and phosphoric acid existing in blood as general biochemical substances are disturbing factors for accurate detection of pyrophosphoric acid generated by polymerase elongation reaction.

(B) Primer complementary with target nucleic acid fragment: A primer complementary with a target nucleic acid fragment used in the present invention is oligonucleotide having a nucleotide sequence complementary with a target site, the nucleotide sequence of the target nucleic acid fragment being known. Hybridization of a primer complementary with the target nucleic acid fragment to a target site of the target nucleic acid fragment results in progress on polymerase elongation reaction starting from the 3' terminus of the primer and using the target nucleic acid as template. Thus, whether or not the primer recognizes and specifically hybridizes to a target site of the target nucleic acid fragment is an important issue in the present invention. The number of nucleotides in the primer used in the present invention is preferably 5 to 60, and particularly preferably 15 to 40. If the number of nucleotides in the primer is too small, specificity with the target site of the target nucleic acid fragment is deteriorated and also a hybrid with the target nucleic acid fragment cannot be stably formed. When the number of nucleotides in the primer is too high, double-strands are disadvantageously formed due to hydrogen bonds between primers or between nucleotides in a primer. This also results in deterioration in specificity.

When the existence of the target nucleic acid fragment is detected by the method according to the present invention, a plurality of primers complementary with each different site in the target nucleic acid fragment can be used. Thus, recognition of the target nucleic acid fragment in a plurality of sites results in improvement in specificity in detecting the existence of the target nucleic acid fragment. When a part of the target nucleic acid fragment is amplified (e.g., PCR), a plurality of primers can be designed in accordance with the amplification methods.

When the nucleotide sequence of the target nucleic acid fragment is detected by the method according to the present invention, particularly when the occurrence of mutation or polymorphisms is detected, a primer is designed in accordance with a type of nucleotide corresponding to mutation or polymorphisms so as to contain a portion of mutation or polymorphisms of interest. Thus, the occurrence of mutation or polymorphisms of the target nucleic acid fragment causes difference in the occurrence of hybridization of the primer to the target nucleic acid fragment, and the detection as difference in polymerase elongation reaction eventually becomes feasible. By setting a portion corresponding to mutation or polymorphisms around the 3' terminus of the primer, difference in recognition of the polymerase reaction site occurs, and this eventually enables the detection as difference in polymerase elongation reaction.

(C) Polymerase: When the target nucleic acid is DNA, polymerase used in the present invention is DNA polymerase which catalyzes complementary elongation reaction which starts from the double-strand portion formed by hybridization of the primer with the target nucleic acid fragment in its portion denatured into single-strand in the 5" 3' direction by using deoxynucleoside triphosphate (dNTP) as material and using the target nucleic acid fragment as template. Specific examples of DNA polymerase used include DNA polymerase I, Klenow fragment of DNA polymerase I, and Bst DNA polymerase. DNA polymerase can be selected or combined depending on the purpose. For example, when a part of the target nucleic acid fragment is amplified (e.g., PCR), use of Taq DNA polymerase which is excellent in heat resistance, is effective. When a part of the target nucleic acid fragment is amplified by using the amplification method (loop-mediated isothermal amplification of DNA (the LAMP method)) described in "BIO INDUSTRY, Vol. 18, No. 2, 2001," use of Bst DNA polymerase is effective as strand displacement-type DNA polymerase which has no nuclease activity in the 5" 3' direction and catalyzes elongation reaction while allowing double-strand DNA to be released as single-strand DNA on the template. Use of DNA polymerase α, T4 DNA polymerase, and T7 DNA polymerase, which have hexokinase activity in the 3" 5' direction in combination is also possible depending on the purpose.

When a genomic nucleic acid of RNA viruses or mRNA is a target nucleic acid fragment, reverse transcriptase having reverse transcription activity can be used. Further, reverse transcriptase can be used in combination with Taq DNA polymerase.

(D) Polymerase elongation reaction: Polymerase elongation reaction in the present invention includes all the complementary elongation reaction of nucleic acids which proceeds by starting from the 3' terminus of a primer complementary with the target nucleic acid fragment as described in (B) above which was specifically hybridized with a part of the portion denatured into a single-strand of the target nucleic acid fragment as described in (A), using deoxynucleoside triphosphate (dNTP) as material, using a polymerase as described in (C) above as a catalyst, and using a target nucleic acid fragment as template. This complementary nucleic acid elongation reaction indicates that continuous elongation reaction occurs at least twice (corresponding to 2 nucleotides).

Examples of a representative polymerase elongation reaction and an amplification reaction of a subject site of the target nucleic acid fragment involving polymerase elongation reaction are shown below. The simplest case is that only one polymerase elongation reaction in the 5" 3' direction is carried out using the target nucleic acid fragment as template. This polymerase elongation reaction can be carried out under isothermal conditions. In this case, the amount of pyrophosphoric acid generated as a result of polymerase elongation reaction is in proportion to the initial amount of the target nucleic acid fragment. Specifically, it is a suitable method for quantitatively detecting the existence of the target nucleic acid fragment.

When the amount of the target nucleic acid is small, a target site of the target nucleic acid is preferably amplified by any means utilizing polymerase elongation reaction. In the amplification of the target nucleic acid, various methods which have been heretofore developed, can be used. The most general and spread method for amplifying the target nucleic acid is polymerase chain reaction (PCR). PCR is a method of amplifying a target portion of the target nucleic acid fragment by repeating periodical processes of denaturing (a step of denaturing a nucleic acid fragment from double-strand to single-strand)' annealing (a step of hybridizing a primer to a nucleic acid fragment denatured into single-strand)' polymerase (Taq DNA polymerase) elongation reaction' denaturing, by periodically controlling the increase and decrease in temperature of the reaction solution. Finally, the target site of the target nucleic acid fragment can be amplified 1,000,000 times as compared to the initial amount. Thus, the amount of accumulated pyrophosphoric acid generated upon polymerase elongation reaction in the amplification process in PCR becomes large, and thereby the detection becomes easy.

A cycling assay method using exonuclease described in Japanese Patent Publication Laying-Open No. 5-130870 is a method for amplifying a target site of the target nucleic acid fragment utilizing polymerase elongation. In this method, a primer is decomposed from a reverse direction by performing polymerase elongation reaction starting from a primer specifically hybridized with a target site of the target nucleic acid fragment, and allowing 5" 3' exonuclease to act. In place of the decomposed primer, a new primer is hybridized, and elongation reaction by DNA polymerase proceeds again. This elongation reaction by polymerase and the decomposition reaction by exonuclease for removing the previously elongated strand are successively and periodically repeated. The elongation reaction by polymerase and the decomposition reaction by exonuclease can be carried out under isothermal conditions. The amount of accumulated pyrophosphoric acid generated in polymerase elongation reaction repeated in this cycling assay method becomes large, and the detection becomes easy.

The LAMP method is a recently developed method for amplifying a target site of the target nucleic acid fragment. This method is carried out by using at least 4 types of primers, which complimentarily recognize at least 6 specific sites of the target nucleic acid fragment, and strand displacement-type Bst DNA polymerase, which has no nuclease activity in the 5" 3' direction and which catalyzes elongation reaction while allowing the double-strand DNA on the template to be released as single-strand DNA. In this method, a target site of the target nucleic acid fragment is amplified as a special structure under isothermal conditions. The amplification efficiency of the LAMP method is high, and the amount of accumulated pyrophosphoric acid generated upon polymerase elongation reaction is very large, and the detection becomes easy.

When the target nucleic acid fragment is a RNA fragment, elongation reaction can be carried out by using reverse transcriptase having reverse transcription activity and using the RNA strand as template. Further, RT-PCR can be utilized where reverse transcriptase is used in combination with Taq DNA polymerase, and reverse transcription (RT) reaction is carried out, followed by PCR. Detection of pyrophosphoric acid generated in the RT reaction or RT-PCR reaction enables the detection of the existence of the RNA fragment of the target nucleic acid fragment. This method is effective when the existence of RNA viruses is detected.

(E) Detection of pyrophosphoric acid (PPi): A method represented by formula 1 has been heretofore known as a method for detecting pyrophosphoric acid (PPi). In this method, pyrophosphoric acid (PPi) is converted into adenosinetriphosphate (ATP) with the aid of sulfurylase, and luminescence generated when adenosinetriphosphate acts on luciferin with the aid of luciferase is detected. Thus, an apparatus capable of measuring luminescence is required for detecting pyrophosphoric acid (PPi) by this method.

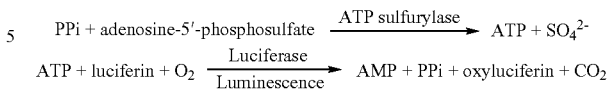

Formula 1

A method for detecting pyrophosphoric acid suitable for the present invention is a method represented by formula 2 or 3. In the method represented by formula 2 or 3, pyrophosphoric acid (PPi) is converted into inorganic phosphate (Pi) with the aid of pyrophosphatase, inorganic phosphate (Pi) is reacted with xanthosine or inosine with the aid of purine nucleoside phosphorylase (PNP), the resulting xanthine or hypoxanthine is oxidated with the aid of xanthine oxidase (XOD) to generate uric acid, and a color developer (a dye precursor) is allowed to develop color with the aid of peroxidase (POD) using hydrogen peroxide ($H_2O_2$) generated in the oxidation process, followed by colorimetry. In the method represented by formula 2 or 3, the result can be detected by colorimetry and, thus, pyrophosphoric acid (PPi) can be detected visually or using a simple colorimetric measuring apparatus.

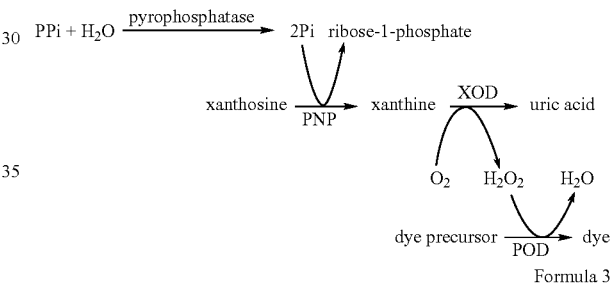

Formula 2

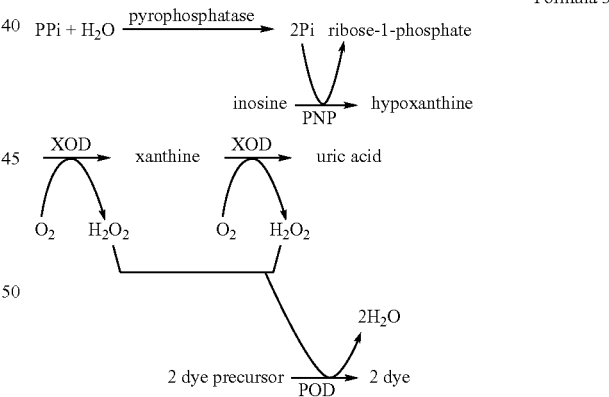

Formula 3

Commercially available pyrophosphatase (EC3, 6, 1, 1), purine nucleoside phosphorylase (PNP, EC2. 4. 2. 1), xanthine oxidase (XOD, EC1. 2. 3. 2), and peroxidase (POD, EC1. 11. 1. 7) can be used. A color developer (i.e., a dye precursor) may be any one as long as it can generate a dye by hydrogen peroxide and peroxidase (POD), and examples thereof which can be used herein include: a composition which generates a dye upon oxidation of leuco dye (e.g., triarylimidazole leuco dye described in U.S. Pat. No. 4,089,747 and the like, diarylimidazole leuco dye described in Japanese Patent Publication Laying-Open No. 59-193352 (EP 0122641A)); and a composition (e.g., 4-aminoantipyrines and phenols or naphthols) containing a compound generating a dye by coupling with other compound upon oxidation.

(F) Dry analytical element: A dry analytical element which can be used in the present invention is an analytical element which comprises a single or a plurality of functional layers, wherein at least one layer (or a plurality of layers) comprises a detection reagent, and a dye generated upon reaction in the layer is subjected to quantification by colorimetry by reflected light or transmitted light from the outside of the analytical element.

In order to perform quantitative analysis using such a dry analytical element, a given amount of liquid sample is spotted onto the surface of a developing layer. The liquid sample spread on the developing layer reaches the reagent layer and reacts with the reagent thereon and develops color. After spotting, the dry analytical element is maintained for a suitable period of time at given temperature (for incubation) and a color developing reaction is allowed to thoroughly proceed. Thereafter, the reagent layer is irradiated with an illuminating light from, for example, a transparent support side, the amount of reflected light in a specific wavelength region is measured to determine the optical density of reflection, and quantitative analysis is carried out based on the previously determined calibration curve.

Since a dry analytical element is stored and kept in a dry state before detection, it is not necessary that a reagent is prepared for each use. As stability of the reagent is generally higher in a dry state, it is better than a so-called wet process in terms of simplicity and swiftness since the wet process requires the preparation of the reagent solution for each use. It is also excellent as an examination method because highly accurate examination can be swiftly carried out with a very small amount of liquid sample.

(G) Dry analytical element for quantifying pyrophosphoric acid: A dry analytical element for quantifying pyrophosphoric acid which can be used in the present invention can have a layer construction which is similar to various known dry analytical elements. The dry analytical element may be multiple layers which contain, in addition to a reagent for performing the reaction represented by formula 2 or 3 according to item (E) above (detection of pyrophosphoric acid (PPi)), a support, a developing layer, a detection layer, a light-shielding layer, an adhesive layer, a water-absorption layer, an undercoating layer, and other layers. Examples of such dry analytical elements include those disclosed in the specifications of Japanese Patent Publication Laying-Open No. 49-53888 (U.S. Pat. No. 3,992,158), Japanese Patent Publication Laying-Open No. 51-40191 (U.S. Pat. No. 4,042,335), Japanese Patent Publication Laying-Open No. 55-164356 (U.S. Pat. No. 4,292,272), and Japanese Patent Publication Laying-Open No. 61-4959 (EPC Publication No. 0166365A).

Examples of the dry analytical element to be used in the present invention include a dry analytical element for quantitative assay of pyrophosphoric acid which has a reagent layer comprising a reagent which converts pyrophosphoric acid into inorganic phosphorus, and a group of reagents capable of color reaction depending on the amount of inorganic phosphorus.

In this dry analytical element for quantitative assay of pyrophosphate, pyrophosphoric acid (PPi) can enzymatically be converted into inorganic phosphorus (Pi) using pyrophosphatase as described above. The subsequent process, that is color reaction depending on the amount of inorganic phosphorus (Pi), can be performed using "quantitative assay method of inorganic phosphorus" (and combinations of individual reactions used therefor), described hereinafter, which is known in the field of biochemical inspection.

It is noted that when representing "inorganic phosphorus," both the expressions "Pi" and "$HPO_4^{2-}$, $H_2PO_4^{1-}$" are used for phosphoric acid (phosphate ion). Although the expression "Pi" is used in the examples of reactions described below, the expression "$HPO_4^{2-}$" may be used for the same reaction formula.

As the quantitative assay method of inorganic phosphorus, an enzyme method and a phosphomolybdate method are known. Hereinafter, this enzyme method and phosphomolybdate method will be described as the quantitative assay method of inorganic phosphorus.

A. Enzyme Method

Depending on the enzyme to be used for the last color reaction during a series of reactions for Pi quantitative detection, the following methods for quantitative assay are available: using peroxidase (POD); or using glucose-6-phosphate dehydrogenase (G6PDH), respectively. Hereinafter, examples of these methods are described.

(1) Example of the Method Using Peroxidase (POD)

(1-1)

Inorganic phosphorus (Pi) is allowed to react with inosine by purine nucleoside phosphorylase (PNP), and the resultant hypoxanthine is oxidized by xanthine oxidase (XOD) to produce uric acid. During this oxidization process, hydrogen peroxide ($H_2O_2$) is produced. Using the thus produced hydrogen peroxide, 4-aminoantipyrines (4-AA) and phenols are subjected to oxidization-condensation by peroxidase (POD) to form a quinonimine dye, which is colorimetrically assessed.

(1-2)

Pyruvic acid is oxidized by pyruvic oxidase (POP) in the presence of inorganic phosphorus (Pi), cocarboxylase (TPP), flavin adenine dinucleotide (FAD) and $Mg^{2+}$ to produce acetyl acetate. During this oxidization process, hydrogen peroxide ($H_2O_2$) is produced. Using the thus produced hydrogen peroxide, 4-aminoantipyrines (4-AA) and phenols are subjected to oxidization-condensation by peroxidase (POD) to form a quinonimine dye which is colorimetrically assessed, in the same manner as described in (1-1).

It is noted that the last color reaction for each of the above processes (1-1) and (1-2) can be performed by a "Trinder reagent" which is known as a detection reagent for hydrogen peroxide. In this reaction, phenols function as "hydrogen donors." Phenols to be used as "hydrogen donors" are classical, and now various modified "hydrogen donors" are used. Examples of these hydrogen donors include N-ethyl-N-sulfopropyl-m-anilidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-sulfopropyl-m-toluidine, N-ethyl-N-(2-hydroxy-3-sulfopropyl)-m-anilidine, N-ethyl-N-(2-hydroxy-3-sulfopropyl)aniline, N-ethyl-N-(2-hydroxy-3-sulfopropyl)-3,5-dimethoxyaniline, N-(2-hydroxy-3-sulfopropyl)-3,5-dimethoxyaniline, N-ethyl-N-(2-hydroxy-3-sulfopropyl)-3,5-dimethylaniline, N-ethyl-N-(2-hydroxy-3-sulfopropyl)-m-toluidine, and N-sulfopropylaniline.

(2) Example of a Method Using glucose-6-phosphate dehydrogenase (G6PDH)

(2-1)

Inorganic phosphorus (Pi) is reacted with glycogen with phosphorylase to produce glucose-1-phosphate (G-1-P). The produced glucose-1-phosphate is converted into glucose-6-phosphate (G-6-P) with phosphoglucomutase (PGM). In the presence of glucose-6-phosphate and nicotiamide adenine dinucleotide (NAD), NAD is reduced to NADH with glucose-6-phosphate dehydrogenase (G6PDH), followed by colorimetric analysis of the produced NADH.

(2-2)

Inorganic phosphorus (Pi) is reacted with maltose with maltose phosphorylase (MP) to produce glucose-1-phosphate (G-1-P). Thereafter, the produced glucose-1-phosphate is converted into glucose-6-phosphate (G-6-P) with phosphoglucomutase (PGM) in the same manner as described in (2-1). In the presence of glucose-6-phosphate and nicotiamide adenine dinucleotide (NAD), NAD is reduced to NADH with glucose-6-phosphate dehydrogenase (G6PDH), followed by colorimetric analysis of the produced NADH.

B. Phosphomolybdate Method

There are two phosphomolybdate methods. One is a direct method wherein "Phosphomolybdates ($H_3[PO_4Mo_{12}O_{36}]$)" prepared by complexing inorganic phosphorus (phosphate) and aqueous molybdate ions under acidic condition are directly quantified. The other is a reduction method wherein further to the above direct method, Mo(IV) is reduced to Mo(III) by a reducing agent and molybudenum blue (Mo(III)) is quantified. Examples of the aqueous molybdate ions include aluminum molybdate, cadmium molybdate, calcium molybdate, barium molybdate, lithium molybdate, potassium molybdate, sodium molybdate, and ammonium molybdate. Representative examples of the reducing agents to be used in the reduction method include 1-amino-2-naphthol4-sulfonic acid, ammonium ferrous sulfate, ferrous chloride, stannous chloride-hydrazine, p-methylaminophenol sulfate, N,N-dimethyl-phenylenediamine, ascorbic acid, and malachite green.

When a light-transmissive and water-impervious support is used, the dry analytical element can be practically constructed as below. However, the scope of the present invention is not limited to these.

(1) One having a reagent layer on the support.

(2) One having a detection layer and a reagent layer in that order on the support.

(3) One having a detection layer, a light reflection layer, and a reagent layer in that order on the support.

(4) One having a second reagent layer, a light reflection layer, and a first reagent layer in that order on the support.

(5) One having a detection layer, a second reagent layer, a light reflection layer, and a first reagent layer in that order on the support.

In (1) to (3) above, the reagent layer may be constituted by a plurality of different layers. For example, a first reagent layer may contain enzyme pyrophosphatase which is required in the pyrophosphatase reaction represented by formula 2 or 3, and substrate xanthosine or substrate inosine and enzyme PNP which are required in the PNP reaction, a second reagent layer may contain enzyme XOD which is required in the XOD reaction represented by formula 2 or 3, and a third reagent layer may contain enzyme POD which is required in the POD reaction represented by formula 2 or 3, and a coloring dye (dye precursor). Alternatively, two reagent layers are provided. On the first reagent layer, the pyrophosphatase reaction and the PNP reaction may be proceeded, and the XOD reaction and the POD reaction may be proceeded on the second reagent layer. Alternatively, the pyrophosphatase reaction, the PNP reaction and the XOD reaction may be proceeded on the first reagent layer, and the POD reaction may be proceeded on the second reagent layer.

A water absorption layer may be provided between a support and a reagent layer or detection layer. A filter layer may be provided between each layer. A developing layer may be provided on the reagent layer and an adhesive layer may be provided therebetween.

Any of light-nontransmissive (opaque), light-semitransmissive (translucent), or light-transmissive (transparent) support can be used. In general, a light-transmissive and water-impervious support is preferred. Preferable materials for a light-transmissive and water-impervious support are polyethylene terephthalate or polystyrene. In order to firmly adhere a hydrophilic layer, an undercoating layer is generally provided or hydrophilization is carried out.

When a porous layer is used as a reagent layer, the porous medium may be a fibrous or nonfibrous substance. Fibrous substances used herein include, for example, filter paper, non-woven fabric, textile fabric (e.g. plain-woven fabric), knitted fabric (e.g., tricot knitted fabric), and glass fiber filter paper. Nonfibrous substances may be any of a membrane filter comprising cellulose acetate etc., described in Japanese Patent Publication Laying-Open No. 49-53888 and the like, or a particulate structure having mutually interconnected spaces comprising fine particles of inorganic substances or organic substances described in, for example, Japanese Patent Publication Laying-Open No. 49-53888, Japanese Patent Publication Laying-Open No. 55-90859 (U.S. Pat. No. 4,258,001), and Japanese Patent Publication Laying-Open No. 58-70163 (U.S. Pat. No. 4,486,537). A partially-adhered laminate which comprises a plurality of porous layers described in, for example, Japanese Patent Publication Laying-Open No. 61-4959 (EP Publication 0166365A), Japanese Patent Publication Laying-Open No. 62-116258, Japanese Patent Publication Laying-Open No. 62-138756 (EP Publication 0226465A), Japanese Patent Publication Laying-Open No. 62-138757 (EP Publication 0226465A), and Japanese Patent Publication Laying-Open No. 62-138758 (EP Publication 0226465A), is also preferred.

A porous layer may be a developing layer having so-called measuring action, which spreads liquid in an area substantially in proportion to the amount of the liquid to be supplied. Preferably, a developing layer is textile fabric, knitted fabric, and the like. Textile fabrics and the like may be subjected to glow discharge treatment as described in Japanese Patent Publication Laying-Open No. 57-66359. A developing layer may comprise hydrophilic polymers or surfactants as described in Japanese Patent Publication Laying-Open No. 60-222770 (EP 0162301A), Japanese Patent Publication Laying-Open No. 63-219397 (German Publication DE 3717913A), Japanese Patent Publication Laying-Open No. 63-112999 (DE 3717913A), and Japanese Patent Publication Laying-Open No. 62-182652 (DE 3717913A) in order to regulate a developing area, a developing speed and the like.

For example, a method is useful where the reagent of the present invention is previously impregnated into or coated on a porous membrane etc., comprising paper, fabric or polymer, followed by adhesion onto another water-pervious layer provided on a support (e.g., a detection layer) by the method as described in Japanese Patent Publication Laying-Open No. 55-1645356.

The thickness of the reagent layer thus prepared is not particularly limited. When it is provided as a coating layer, the thickness is suitably in the range of about 1 μm to 50 μm, preferably in the range of 2 μm to 30 μm. When the reagent layer is provided by a method other than coating, such as lamination, the thickness can be significantly varied in the range of several tens of to several hundred μm.

When a reagent layer is constituted by a water-pervious layer of hydrophilic polymer binders, examples of hydrophilic polymers which can be used include: gelatin and a derivative thereof (e.g., phthalated gelatin); a cellulose derivative (e.g., hydroxyethyl cellulose); agarose, sodium arginate; an acrylamide copolymer or a methacrylamide copolymer (e.g., a copolymer of acrylamide or methacrylamide and various vinyl monomers); polyhydroxyethyl methacrylate; polyvinyl alcohol; polyvinyl pyrrolidone; sodium polyacrylate; and a copolymer of acrylic acid and various vinyl monomers.

A reagent layer composed of hydrophilic polymer binders can be provided by coating an aqueous solution or water dispersion containing the reagent composition of the present invention and hydrophilic polymers on the support or another layer such as a detection layer followed by drying the coating in accordance with the methods described in the specifications of Japanese Patent Examined Publication No. 53-21677 (U.S. Pat. No. 3,992,158), Japanese Patent Publication Laying-Open No. 55-164356 (U.S. Pat. No. 4,292,272), Japanese Patent Publication Laying-Open No. 54-101398 (U.S. Pat. No. 4,132,528) and the like. The thickness of the reagent layer comprising hydrophilic polymers as binders is about 2 µm to about 50 µm, preferably about 4 µm to about 30 µm on a dry basis, and the coverage is about 2 g/m² to about 50 g/m², preferably about 4 g/m² to about 30 g/m².

The reagent layer can further comprise an enzyme activator, a coenzyme, a surfactant, a pH buffer composition, an impalpable powder, an antioxidant, and various additives comprising organic or inorganic substances in addition to the reagent composition represented by formula 2 or 3 in order to improve coating properties and other various properties of diffusible compounds such as diffusibility, reactivity, and storage properties. Examples of buffers which can be contained in the reagent layer include pH buffer systems described in "Kagaku Binran Kiso (Handbook on Chemistry, Basic)," The Chemical Society of Japan (ed.), Maruzen Co., Ltd. (1996), p. 1312-1320, "Data for Biochemical Research, Second Edition, R. M. C. Dawson et al. ($2^{nd}$ ed.), Oxford at the Clarendon Press (1969), p. 476-508, "Biochemistry" 5, p. 467-477 (1966), and "Analytical Biochemistry" 104, p. 300-310 (1980). Specific examples of pH buffer systems include a buffer containing borate; a buffer containing citric acid or citrate; a buffer containing glycine, a buffer containing bicine; a buffer containing HEPES; and Good's buffers such as a buffer containing MES. A buffer containing phosphate cannot be used for a dry analytical element for detecting pyrophosphoric acid.

The dry analytical element for quantifying pyrophosphoric acid which can be used in the present invention can be prepared in accordance with a known method disclosed in the above-described various patent specifications. The dry analytical element for quantifying pyrophosphoric acid is cut into small fragments, such as, an about 5 mm to about 30 mm-square or a circle having substantially the same size, accommodated in the slide frame described in, for example, Japanese Patent Examined Publication No. 57-283331 (U.S. Pat. No. 4,169,751), Japanese Utility Model Publication Laying-Open No. 56-142454 (U.S. Pat. No. 4,387,990), Japanese Patent Publication Laying-Open No. 57-63452, Japanese Utility Model Publication Laying-Open No. 58-32350, and Japanese Patent Publication Laying-Open No. 58-501144 (International Publication WO 083/00391), and used as slides for chemical analysis. This is preferable from the viewpoints of production, packaging, transportation, storage, measuring operation, and the like. Depending on its intended use, the analytical element can be accommodated as a long tape in a cassette or magazine, as small pieces accommodated in a container having an opening, as small pieces applied onto or accommodated in an open card, or as small pieces cut to be used in that state.

The dry analytical element for quantifying pyrophosphoric acid which can be used in the present invention can quantitatively detect pyrophosphoric acid which is a test substance in a liquid sample, by operations similar to that described in the above-described patent specifications and the like. For example, about 2 µL to about 30 µL, preferably 4 µL to 15 µL of aqueous liquid sample solution is spotted on the reagent layer. The spotted analytical element is incubated at constant temperature of about 20° C. to about 45° C., preferably about 30° C. to about 40° C. for 1 to 10 minutes. Coloring or discoloration in the analytical element is measured by the reflection from the light-transmissive support side, and the amount of pyrophosphoric acid in the specimen can be determined based on the principle of colorimetry using the previously prepared calibration curve. Quantitative analysis can be carried out with high accuracy by keeping the amount of liquid sample to be spotted, the incubation time, and the temperate at constant levels.

Quantitative analysis can be carried out with high accuracy in a very simple operation using chemical analyzers described in, for example, Japanese Patent Publication Laying-Open No. 60-125543, Japanese Patent Publication Laying-Open No. 60-220862, Japanese Patent Publication Laying-Open No. 61-294367, and Japanese Patent Publication Laying-Open No. 58-161867 (U.S. Pat. No. 4,424,191). Semiquantitative measurement may be carried out by visually judging the level of coloring depending on the purpose and accuracy needed.

Since the dry analytical element for quantifying pyrophosphoric acid which can be used in the present invention is stored and kept in a dry state before analysis, it is not necessary that a reagent is prepared for each use, and stability of the reagent is generally higher in a dry state. Thus, in terms of simplicity and swiftness, it is better than a so-called wet process, which requires the preparation of the reagent solution for each use. It is also excellent as an examination method because highly accurate examination can be swiftly carried out with a very small amount of liquid sample.

The dry analytical element for quantifying inorganic phosphorus which can be used in the second aspect of the present invention can be prepared by removing pyrophosphatase from the reagent layer in the aforementioned dry analytical element for quantifying pyrophosphoric acid. The dry analytical element described in Japanese Patent Publication Laying-Open No. 7-197 can also be used. The dry analytical element for quantifying inorganic phosphorus is similar to the aforementioned dry analytical element for quantifying pyrophosphoric acid in its layer construction, method of production, and method of application, with the exception that the reagent layer does not comprise pyrophosphatase.

The present invention will be described further in detail with reference to examples below, but the present invention is not limited by the examples.

EXAMPLES

Example 1

(1) Materials and Reagents

A cartridge for purifying nucleic acids (which is connected with a pressure sensor by Keyence Corporation (product name: pressure sensor AP34A)), whose structure is shown in FIGS. 1 to 6, is used. From the second opening part side, a sample, a washing solution and distilled water are charged in turn, each time the piston member (plunger) being inserted and pushed. Fuji Microfilter FR250 (made by Fuji Photo Film Co., Ltd.) was used as a nucleic acid-adsorbing solid phase. An adsorption buffer solution for purifying nucleic acids and a washing buffer solution were prepared in the following manner.

| Adsorption buffer | |
| --- | --- |
| guanidine hydrochloride (made by Life Technology, Inc.) | 382 g |
| Tris (made by Life Technology, Inc.) | 12.1 g |
| Triton-X100 (made by ICN) | 10 g |
| Distilled water | 1,000 ml |
| Washing buffer | |
| 10 mM Tris-HCl | 65% ethanol |

(2) Nucleic Acid-Purifying Operation

Sample solutions (5 types) with different viscosity each containing a specific amount of DNA were prepared. To 200 µl of each sample solution were added 200 µl of the adsorption buffer and 200 µl of protease K, and the mixture was incubated at 60° C. for 10 minutes. After the incubation, 200 µl of ethanol was added and stirred. After the stirring, this liquid was charged into a cartridge for purifying nucleic acids with a pressure sensor, whose structure is shown in FIGS. 1 to 6. After the charge, the liquid was extruded by a piston. Immediately after the total amount of the liquid is extruded, the operation for extruding the liquid by the piston was stopped by the pressure sensor. In addition, as a comparative example, using the same sample solutions (5 types), similar operation to the above was performed using a cartridge for purifying nucleic acids provided with no pressure sensor. In this case, the extruding operation by the piston was performed for a fixed period of time (30 seconds).

Subsequently, 500 µl of the washing buffer was charged, and impurities on the cartridge and the adsorbing solid phase were washed by extruding the liquid by a piston. Finally, 200 µl of distilled water was charged and the liquid was recovered as a DNA solution by extruding the liquid by a piston. At this time too, immediately after the total amount of the liquid is extruded, the operation for extruding the liquid by the piston was stopped by the pressure sensor. In addition, as a comparative example, similar operation to the above was performed using a cartridge for purifying nucleic acids provided with no pressure sensor. In the comparative example, the extruding operation by the piston was performed for a fixed period of time (30 seconds).

(3) Quantitative Determination of the Recovered Amount of Nucleic Acids

The yield of the DNA purified by the operation of (2) and the operation time (the time from the start of charging the sample solution until the recovery of the DNA solution is completed) is shown in Table 1 below. The results shown in Table 1 indicate that the operation time can be reduced by the present invention.

TABLE 1

| Sample No. | DNA (µg) | Operation Time |
| --- | --- | --- |
| 1 (present invention) | 6.2 | 110 seconds |
| 2 (present invention) | 4.6 | 96 seconds |
| 3 (present invention) | 3.7 | 83 seconds |
| 4 (present invention) | 2.3 | 62 seconds |
| 5 (present invention) | 0 | 55 seconds |
| 1 (comparative example) | 5.0 | 130 seconds |
| 2 (comparative example) | 4.5 | 130 seconds |
| 3 (comparative example) | 3.9 | 130 seconds |
| 4 (comparative example) | 2.4 | 130 seconds |
| 5 (comparative example) | 0 | 130 seconds |

Example 2

(1) Manufacture of a Container

A container for the apparatus for separating and purifying nucleic acid was made by high-impact polystyrene. The container has a part for accommodating the solid phase for adsorbing nucleic acid with an internal diameter of 7 mm and a thickness of 2 mm.

(2) Manufacture of the Apparatus for Separating and Purifying Nucleic Acid

One sheet of a porous film of triacetyl cellulose with a saponification rate of 100% [saponified product of Microfilter FM500 (made by Fuji Photo Film Co., Ltd.)] was used as a solid phase for separating and purifying nucleic acids of the present invention. The solid phase was accommodated in the accommodation part of the container manufactured in the above (1) to manufacture the apparatus for separating and purifying nucleic acids.

(3) Preparation of Nucleic Acid Adsorption Buffer Solution and Washing Buffer Solution Nucleic acid adsorption buffer solution and washing buffer solution having formulations shown in Table 1 were prepared.

| Nucleic acid adsorption buffer | |
| --- | --- |
| guanidine hydrochloride (made by Life Technology, Inc.) | 382 g |
| Tris (made by Life Technology, Inc.) | 12.1 g |
| Triton-X100 (made by ICN) | 10 g |
| Distilled water | 1,000 ml |
| Washing buffer | |
| 10 mM Tris-HCl | 65% ethanol |

(4) Nucleic Acid Purifying Operation

To 200 µl of human whole blood which was drawn using a blood vacuum tube, 200 µl of the nucleic acid adsorption buffer solution having the formulation shown in Table 1 and 20 µl of protease K were added, and the mixture was incubated at 60° C. for 10 minutes. After the incubation, 200 µl of ethanol was added and stirred. After the stirring, the whole blood sample solution treated in the manner described above was charged from the upper opening of the apparatus for separating and purifying nucleic acids manufactured in (2). Then, in the present invention, the inside of the container was pressurized from 0 kpa to 60 kpa over 15 seconds to discharge the liquid in the container. In this case, almost total amount of the sample solution was discharged from the container.

On the other hand, as a comparative example, the whole blood sample was charged from the upper opening of the apparatus for separating and purifying nucleic acids manufactured in (2) in the same manner as described above. Then, the inside of the container was pressurized from 0 kpa to 110 kpa in 2 seconds to discharge the liquid in the container. In this case, a part of the sample solution is remained in the container as droplets.

In the present invention, 1 ml of the nucleic acid washing buffer solution was charged from the upper opening of the apparatus immediately after the discharge. Then, the inside of the container was pressurized from 0 kpa to 60 kpa over 15 seconds to discharge the liquid in the container to wash the inside of the container in the same manner as described above. After washing, 200 µl of purified distilled water was charged from the upper opening of the apparatus. Then, the inside of the container was pressurized from 0 kpa to 60 kpa over 15 seconds to discharge the distilled water to recover the discharged liquid in the same manner as described above.

On the other hand, in the comparative example, the inside of the container was pressurized from 0 kpa to 110 kpa in 2 seconds instead of pressurizing the inside of the container from 0 kpa to 60 kpa over 15 seconds in the above operation.

(5) Quantitative Determination of the Recovered Amount of Nucleic Acids, and Determination of Impurities The absorbance of the above discharged liquid recovered was measured to quantitatively determine the recovered amount of nucleic acids and impurities (hemoglobin). The recovered amount of nucleic acids was quantitatively determined by the measurement of optical absorption at a wavelength of 260 nm, and the impurities (hemoglobin) were quantitatively determined by the measurement of optical absorption at 400 nm. The results are shown in Table 2. From the results in Table 2, it can be understood that the pressurizing method of the present invention provides a higher recovered amount of DNA and fewer impurities (hemoglobin).

TABLE 2

Recovered amount of nucleic acids and impurities

| | Present Invention | Comparative Example |
|---|---|---|
| Recovered amount of DNA | 4.2 µg | 3.9 µg |
| Impurities (Optical absorption at 400 nm) | 0.003 | 0.53 |

Effect of the Invention

The use of the apparatus for separating and purifying nucleic acids of the present invention allows efficient separation of highly pure nucleic acids from a sample solution containing nucleic acids in a shorter time than before. Further, the apparatus for separating and purifying nucleic acids of the present invention allows efficient separation of highly pure nucleic acids from a sample solution containing nucleic acids using a solid phase which is excellent in separation performance, has good washing efficiency, is easy to process, has substantially the same separation performance and can be produced in large amounts.

Further, according to the present invention, the sample solution can be prevented from remaining in the container by a method for purifying nucleic acids comprising a step of pressurizing a nucleic acid-containing sample solution in a container to pass the above sample solution through a solid phase located in the container to adsorb the nucleic acids to the solid phase. Therefore, the use of the method for separating and purifying nucleic acids of the present invention allows a high-yield isolation and purification of highly pure nucleic acids from the sample solution.

The invention claimed is:

1. An apparatus for separating and purifying nucleic acids comprising:
    a cylindrical syringe having a leading end part in which a first opening part comprising an opening is formed, a base end part in which a second opening part comprising an opening is formed and an accommodation part between said first opening part and said second opening part, the accommodation part being able to hold a sample solution therein;
    a solid phase-holding member comprising a column with a circular shape, wherein the column comprises a top portion, a middle portion, and a bottom portion having a flow hole, and connects to said leading end part of said cylindrical syringe by the top portion of the column such that a part of the first opening part of the syringe is inside the column;
    a solid phase comprising an organic polymer having a hydroxyl group on the surface thereof, wherein the solid phase is accommodated in said solid phase-holding member, located only at the interior of the bottom portion of the column of the solid phase-holding member and contacts with the opening of the first opening part of the leading end part of the cylindrical syringe at the interior of the column, and adsorbs and desorbs nucleic acids in the sample solution;
    a pressure difference-generating apparatus, and
    a pressure sensor capable of detecting the pressure in the accommodation part being connected to an operation part of the pressure difference-generating apparatus which couples to the opening of the second opening part.

2. The apparatus for separating and purifying nucleic acids according to claim 1, wherein the pressure difference-generating apparatus is a piston member comprising a plunger extending from said second opening part into said accommodation part when the plunger is plunged into the inside of the accommodation part.

3. The apparatus for separating and purifying nucleic acids according to claim 2 further comprises a liquid-tight member located at the leading end of said plunger, wherein the liquid-tight member can be brought into close contact with the inner surface of said accommodation part and is slidable in said accommodation part.

4. The apparatus for separating and purifying nucleic acids according to claim 2, wherein said piston member further comprises a check valve that is closed when said piston member is moved to the leading end part of the syringe and that is open when said piston member is moved to the base end part of the syringe.

5. The apparatus for separating and purifying nucleic acids according to claim 1, wherein the pressure difference-generating apparatus is a pump that is capable of putting the inside of the accommodation part of the syringe into a pressurized state.

6. The apparatus for separating and purifying nucleic acids according to claim 1, wherein a circular solid phase-supporting surface is formed on the inner surface of the bottom portion of the column of said solid phase-holding member, the solid phase-supporting surface being generally perpendicular to the longitudinal axis of said syringe;
    said solid phase is formed in a circular shape and is placed in a direction parallel to said solid phase-supporting surface; the leading end of the leading end part of said syringe is formed in a circular shape and is abutted to the immediate inside of the circular peripheral edge of said solid phase to press the solid phase to the side of said solid phase-supporting surface.

7. The apparatus for separating and purifying nucleic acids according to claim 1, wherein the organic polymer having a hydroxyl group on the surface thereof is a surface saponification product of acetyl cellulose.

8. The apparatus for separating and purifying nucleic acids according to claim 1, wherein the organic polymer having a hydroxyl group on the surface thereof is a surface saponification product of triacetyl cellulose.

9. The apparatus for separating and purifying nucleic acids according to claim 7, wherein the surface saponification rate of the surface saponification product of acetyl cellulose is 5% or more.

10. The apparatus for separating and purifying nucleic acids according to claim 7, wherein the surface saponification rate of the surface saponification product of acetyl cellulose is 10% or more.

11. The apparatus for separating and purifying nucleic acids according to claim 7, wherein the acetyl cellulose is formed into a porous film or a non-porous film.

12. The apparatus for separating and purifying nucleic acids according to claim 1, wherein when said pressure sensor detects a certain preset pressure inside the accommodation part, it sends a signal for stopping the pressurization to the pressure difference generating apparatus, and thereby the pressurization inside the accommodation part is stopped.

13. A method for separating and purifying nucleic acids comprising adsorbing and desorbing the nucleic acids in a sample solution on a solid phase having an organic polymer having a hydroxyl group on the surface thereof and separating and purifying the nucleic acids by using the apparatus of claim 1.

14. The method for separating and purifying nucleic acids according to claim 13, wherein the pressure sensor capable of detecting the pressure in the accommodation part is used to monitor the pressure in the accommodation part, and the discharge of the sample solution in the accommodation part can be sensed by a pressure change.

15. The method for separating and purifying nucleic acids according to claim 13, wherein the sample solution is a solution which is prepared by adding a water soluble organic solvent to a solution obtained by treating a specimen containing a cell or a virus with a nucleic acid-solubilizing reagent.

16. The method for separating and purifying nucleic acids according to claim 15, wherein the nucleic acid-solubilizing reagent is a guanidine salt or a surfactant or a protease.

17. The method for separating and purifying nucleic acids according to claim 13 further comprising washing the solid phase using a nucleic acid washing buffer and said desorbing comprising desorbing the nucleic acids adsorbed on the solid phase using a liquid capable of desorbing the nucleic acids adsorbed on the solid phase.

18. The method for separating and purifying nucleic acids according to claim 17, wherein the nucleic acid washing buffer is a solution containing methanol or ethanol or isopropanol or n-propanol or mixture thereof in a concentration of 20 to 100% based on percentage by weight.

19. The method for separating and purifying nucleic acids according to claim 17, wherein the liquid capable of desorbing the nucleic acids adsorbed on the solid phase is a solution having a salt concentration of 0.5 M or less.

20. The method for separating and purifying nucleic acids according to claim 13, wherein said adsorbing and desorbing the nucleic acids further comprising the steps of:
(a) preparing the sample solution containing the nucleic acids from a specimen, and charging said sample solution containing the nucleic acids from the opening of the second opening part of the syringe into said accommodation part of the syringe;
(b) pressurizing the inside of said accommodation part of the the syringe and discharging the charged sample solution containing the nucleic acids from the opening of the first opening part of the syringe to bring the charged sample solution into contact with the solid phase comprising an organic polymer having a hydroxyl group on the surface thereof;
(c) charging a nucleic acid washing buffer from the opening of said second opening part of the syringe;
(d) pressurizing the inside of said accommodation part of the the syringe and discharging the charged nucleic acid washing buffer from said opening of the first opening part of the syringe to bring the charged nucleic acid washing buffer into contact with the solid phase comprising an organic polymer having a hydroxyl group on the surface thereof;
(e) charging a liquid capable of desorbing the nucleic acids adsorbed on the solid phase comprising an organic polymer having a hydroxyl group on the surface thereof from the opening of said second opening part of the syringe; and
(f) pressurizing the inside of said accommodation part of the syringe, discharging the charged liquid capable of desorbing the nucleic acids from said opening of the first opening part of the syringe, desorbing the nucleic acids adsorbed on the solid phase comprising an organic polymer having a hydroxyl group on the surface thereof and discharge the nucleic acids to the outside of the apparatus for separating and purifying nucleic acids.

21. The method for separating and purifying nucleic acids according to claim 20, wherein in steps (b), (d) and (f), the pressure sensor capable of detecting the pressure in the accommodation part of the syringe is used to monitor the pressure in the accommodation part to sense the discharge of the charged sample solution in step (b) or the charged nucleic acid washing buffer in step (d) or the charged liquid capable of desorbing nucleic acids in step (f) in the accommodation part by a pressure change, and wherein steps (c) and (e) start after sensing the discharge of the charged sample solution in step (b) or the charged nucleic acid washing buffer in step (d).

22. The method for separating and purifying nucleic acids according to claim 20, wherein the pressurizing of the inside of said accommodation part in step (b) is stopped when the pressure detected by the pressure sensor reaches a certain level.

23. The method for separating and purifying nucleic acids according to claim 22, wherein when a certain pressure is set inside the accommodation part, no sample solution remains inside the accommodation part.

24. The method for separating and purifying nucleic acids according to claim 20, wherein the pressurization in step (d) and/or step (f) are/is stopped when the pressure detected by the pressure sensor reaches a certain level.

25. The method for separating and purifying nucleic acids according to claim 24, wherein a certain pressure is set so that no sample solution remains in the accommodation part.

26. The method for separating and purifying nucleic acids according to claim 24, wherein the pressure sensor is used to detect whether the pressure in the accommodation part has reached a certain level.

27. A device for separating and purifying nucleic acids comprising a combination of at least two or more apparatuses for separating and purifying nucleic acids, wherein each of said apparatuses comprises a pressure sensor, and the pressure in the accommodation part of each of said apparatuses can be independently detected, wherein each of said apparatuses is an apparatus for separating and purifying nucleic acids, which comprises:

a cylindrical syringe having a leading end part in which a first opening part comprising an opening is formed, a base end part in which a second opening part comprising an opening is formed and an accommodation part between said first opening part and said second opening part, the accommodation part being able to hold a sample solution therein;

a solid phase-holding member comprising a column with a circular shape, wherein the column comprises a top portion, a middle portion, and a bottom portion having a flow hole, and connects to said leading end part of said cylindrical syringe by the top portion of the column such that a part of the first opening part of the syringe is inside the column;

a solid phase comprising an organic polymer having a hydroxyl group on the surface thereof, wherein the solid phase is accommodated in said solid phase-holding member, located only at the interior of the bottom portion of the column of the solid phase-holding member and contacts with the opening of the first opening part of the leading end part of the cylindrical syringe at the interior of the column, and adsorbs and desorbs nucleic acids in the sample solution; and a pressure difference-generating apparatus, wherein the pressure sensor capable of detecting the pressure in the accommodation part is connected to an operation part of the pressure difference-generating apparatus which couples to the opening of the second opening part.

28. The apparatus for separating and purifying nucleic acids according to claim 27, wherein the pressure difference-generating apparatus is a piston member comprising a plunger extending from said second opening part into said accommodation part when the plunger is plunged into the inside of the accommodation part.

29. The apparatus for separating and purifying nucleic acids according to claim 28 further comprises a liquid-tight member located at the leading end of said plunger, wherein the liquid-tight member can be brought into close contact with the inner surface of said accommodation part and is slidable in said accommodation part.

30. The apparatus for separating and purifying nucleic acids according to claim 28, wherein said piston member further comprises a check valve that is closed when said piston member is moved to the leading end part of the syringe and that is open when said piston member is moved to the base end part of the syringe.

31. The apparatus for separating and purifying nucleic acids according to claim 27, wherein when said pressure sensor detects a certain preset pressure inside the accommodation part, it sends a signal for stopping the pressurization to the pressure difference generating apparatus, and thereby the pressurization inside the accommodation part is stopped.

* * * * *